(12) United States Patent
Dunlop et al.

(10) Patent No.: US 11,298,167 B2
(45) Date of Patent: Apr. 12, 2022

(54) TIBIAL PLATEAU LEVELING OSTEOTOMY PLATE

(71) Applicant: ARTHREX, INC., Naples, FL (US)

(72) Inventors: James R. Dunlop, Cape Coral, FL (US); Gregory Joshua Karnes, Naples, FL (US); Brandon L. Roller, Naples, FL (US); Antonio Pozzi, Gainsville, FL (US); James L. Cook, Columbia, MO (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 17/348,888

(22) Filed: Jun. 16, 2021

(65) Prior Publication Data

US 2021/0307797 A1 Oct. 7, 2021

Related U.S. Application Data

(63) Continuation of application No. 16/420,602, filed on May 23, 2019, now Pat. No. 11,096,729, which is a continuation of application No. 14/533,768, filed on Nov. 5, 2014, now Pat. No. 10,299,841.

(60) Provisional application No. 61/900,123, filed on Nov. 5, 2013.

(51) Int. Cl.
*A61B 17/80* (2006.01)
*A61B 17/17* (2006.01)
*A61B 17/84* (2006.01)

(52) U.S. Cl.
CPC ...... *A61B 17/8061* (2013.01); *A61B 17/1764* (2013.01); *A61B 17/80* (2013.01); *A61B 17/842* (2013.01)

(58) Field of Classification Search
CPC .... A61B 17/8061; A61B 17/808; A61B 17/80
See application file for complete search history.

(56) References Cited

U.S. PATENT DOCUMENTS

| | | | |
|---|---|---|---|
| 3,896,500 A | 7/1975 | Rambert et al. | |
| 6,514,274 B1 | 2/2003 | Boucher et al. | |
| 2002/0156474 A1* | 10/2002 | Wack | A61B 17/1728 606/281 |
| 2003/0050666 A1 | 3/2003 | Grafton | |
| 2004/0153073 A1 | 8/2004 | Orbay | |
| 2004/0225291 A1 | 11/2004 | Schwammberger et al. | |
| 2005/0033365 A1 | 2/2005 | Courage | |
| 2005/0049594 A1 | 3/2005 | Wack et al. | |

(Continued)

FOREIGN PATENT DOCUMENTS

WO 01/19267 A1 3/2001

*Primary Examiner* — Amy R Sipp
(74) *Attorney, Agent, or Firm* — Carlson, Gaskey & Olds, P.C.

(57) ABSTRACT

A TPLO plate configured to accommodate flexible strands (flexible loops) attached to tissue to be attached to bone. The TPLO plate has one or more suture eyelets, to allow the user (surgeon) to pass a flexible strand through the eyelets and attach/reattach the tissue to the plate at the anatomical location, and to improve the rotational stability of the joint or bone. The eyelets may have various shapes, forms and configurations and may be provided on or within a surface of the TPLO bone plate in any number, depending on the characteristics of the fractured bone or bone segments, or of the plate design. The eyelets preferably receive one or more flexible strands.

19 Claims, 27 Drawing Sheets

(56) References Cited

U.S. PATENT DOCUMENTS

| | | | |
|---|---|---|---|
| 2005/0240187 A1 | 10/2005 | Huebner et al. | |
| 2006/0173458 A1 | 8/2006 | Forstein et al. | |
| 2006/0264947 A1 | 11/2006 | Orbay et al. | |
| 2006/0276896 A1 | 12/2006 | Fallin et al. | |
| 2007/0135839 A1 | 6/2007 | Cook et al. | |
| 2007/0173843 A1 | 7/2007 | Matityahu | |
| 2007/0233106 A1* | 10/2007 | Horan | A61B 17/8061 606/282 |
| 2008/0300637 A1* | 12/2008 | Austin | A61B 17/8605 606/290 |
| 2009/0216270 A1 | 8/2009 | Humphrey | |
| 2010/0016858 A1 | 1/2010 | Michel | |
| 2010/0030276 A1 | 2/2010 | Huebner et al. | |
| 2011/0137314 A1 | 6/2011 | Kuster et al. | |
| 2011/0224734 A1 | 9/2011 | Schelling | |
| 2011/0224736 A1 | 9/2011 | Humphrey | |
| 2011/0319945 A1 | 12/2011 | Tepic | |
| 2012/0065732 A1 | 3/2012 | Roller et al. | |
| 2012/0123474 A1 | 5/2012 | Zajac et al. | |
| 2012/0310279 A1 | 12/2012 | Sikora et al. | |
| 2013/0096629 A1 | 4/2013 | Rollinghoff et al. | |
| 2013/0204307 A1* | 8/2013 | Castaneda | A61B 17/8061 606/297 |
| 2013/0238032 A1 | 9/2013 | Schilter | |
| 2013/0325011 A1 | 12/2013 | Cleveland et al. | |
| 2014/0180343 A1 | 6/2014 | Gaudin | |

\* cited by examiner

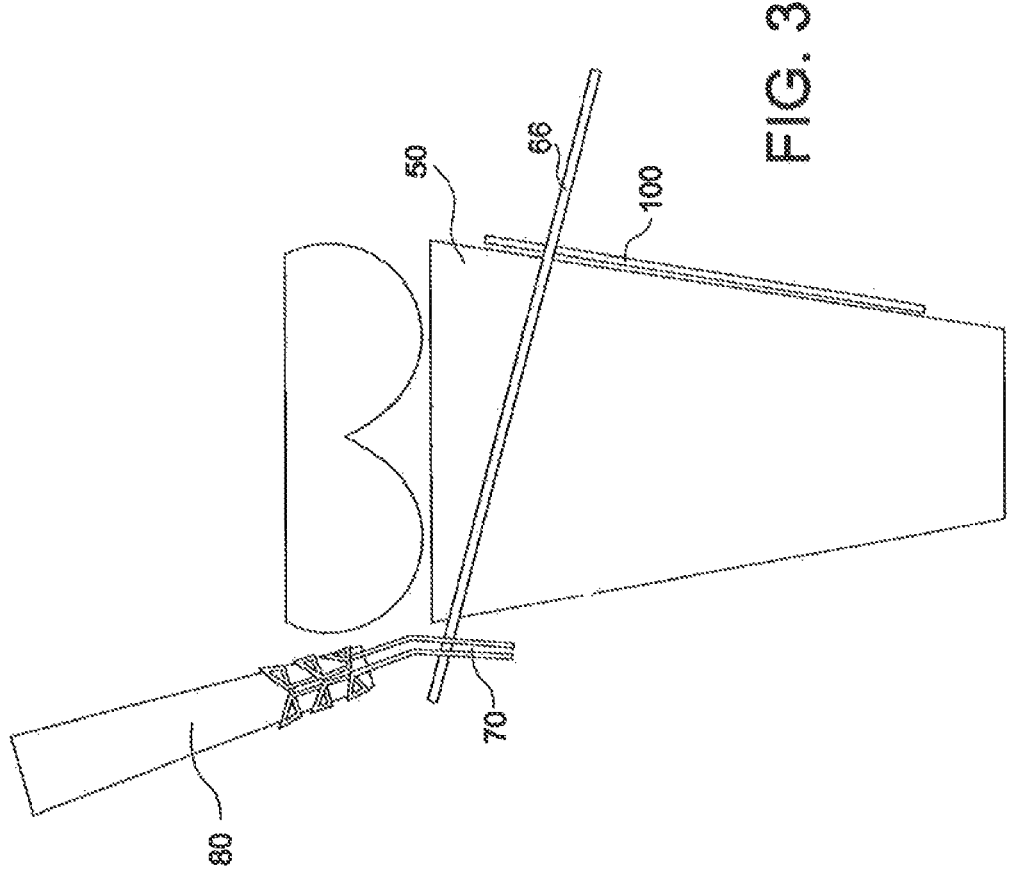

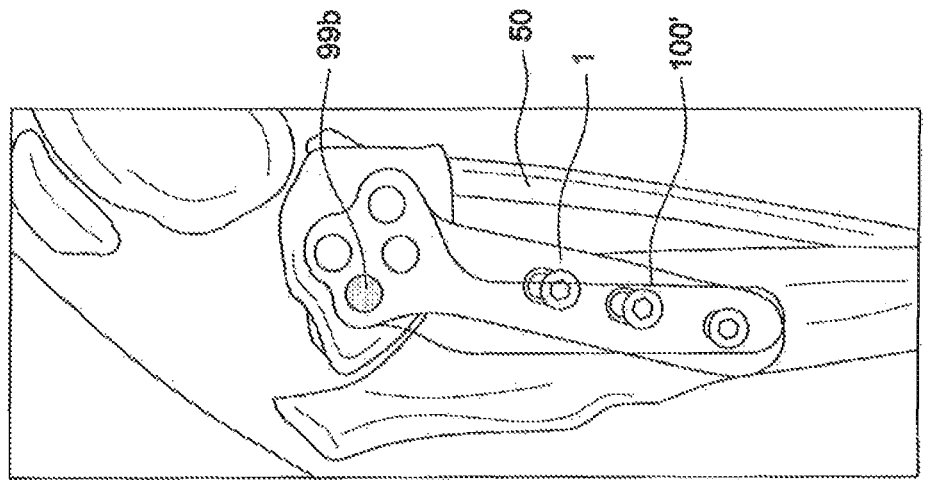
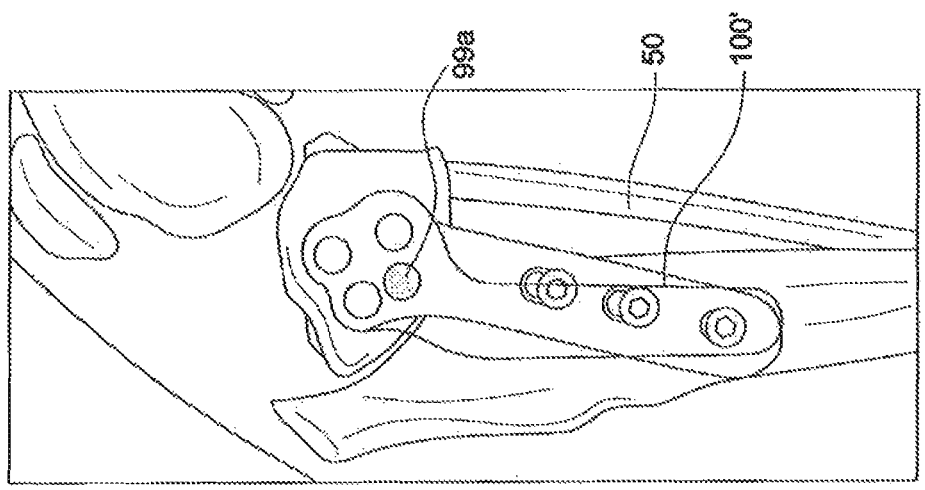
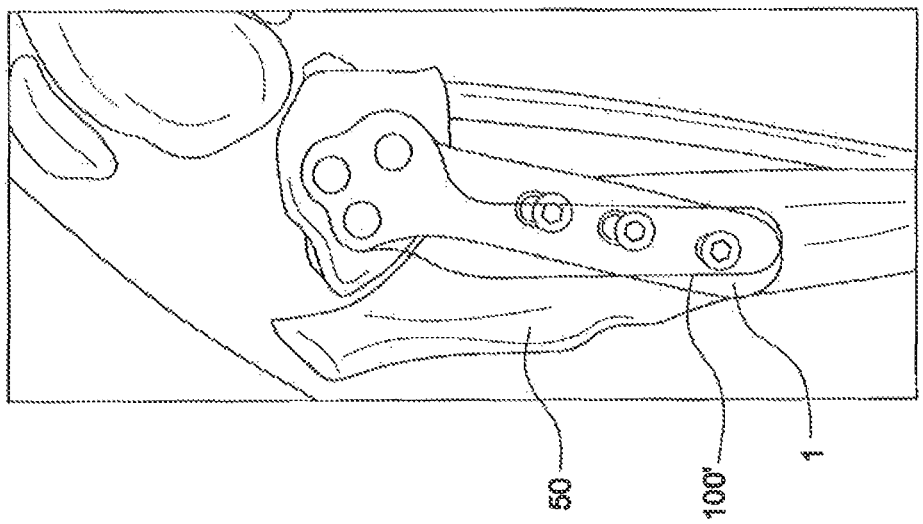

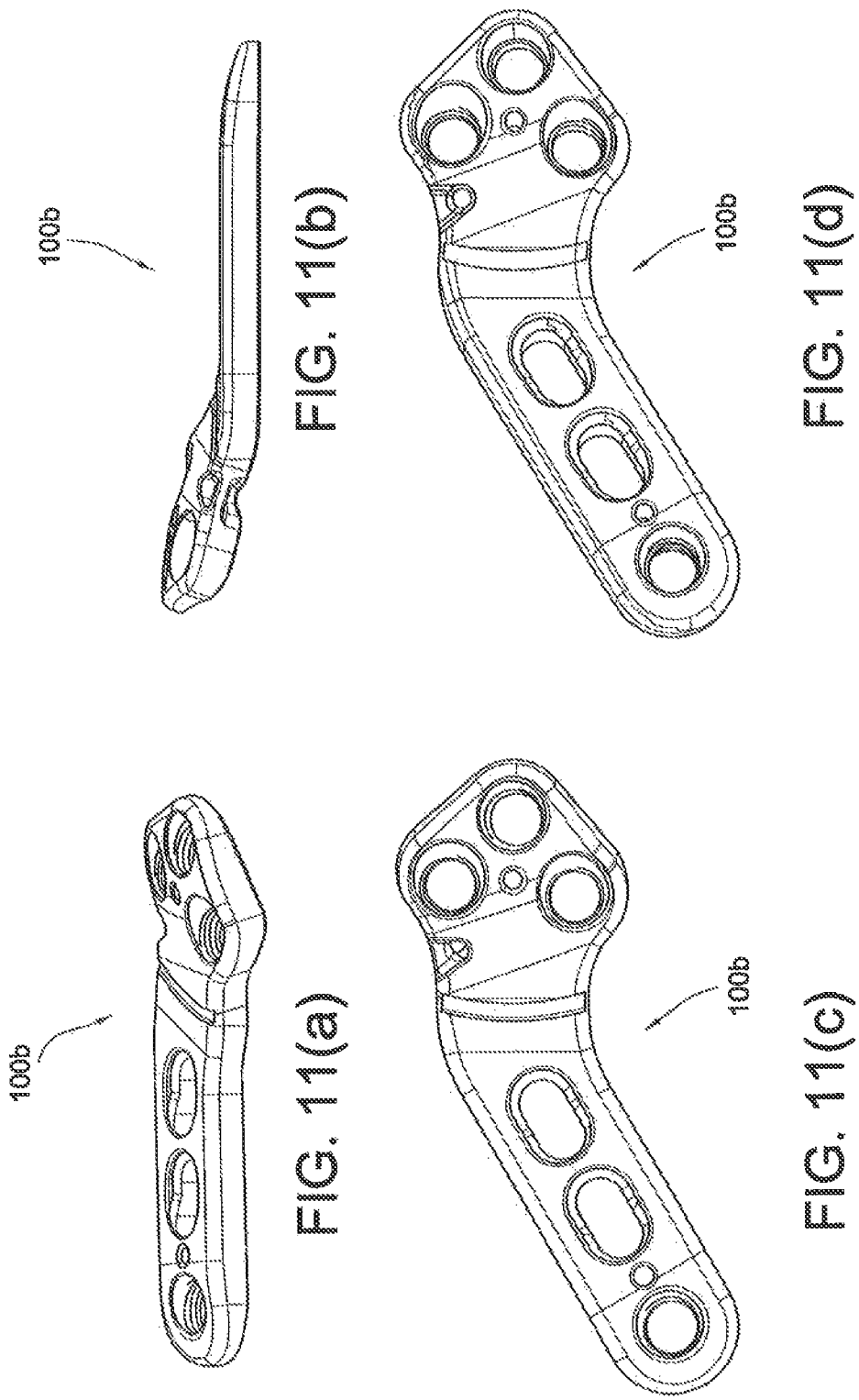

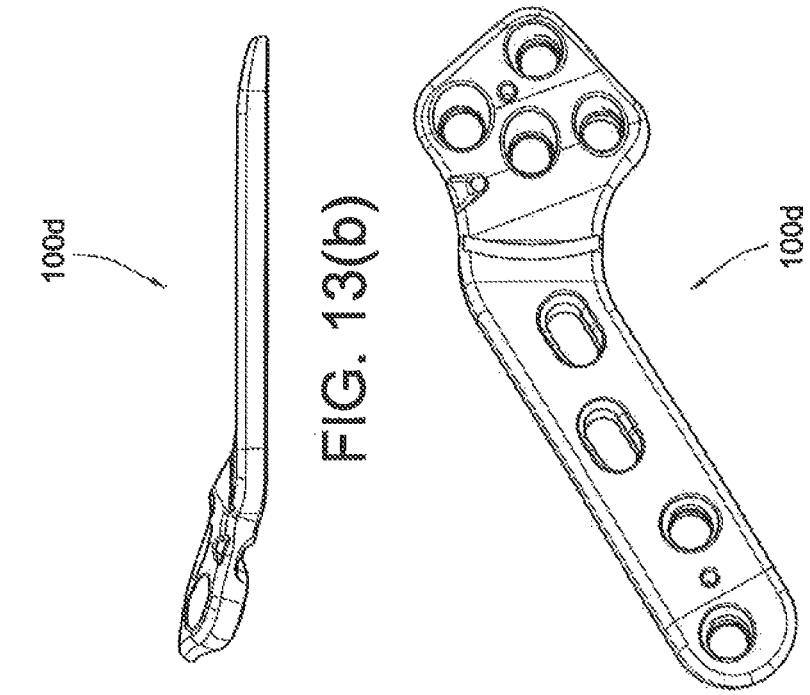
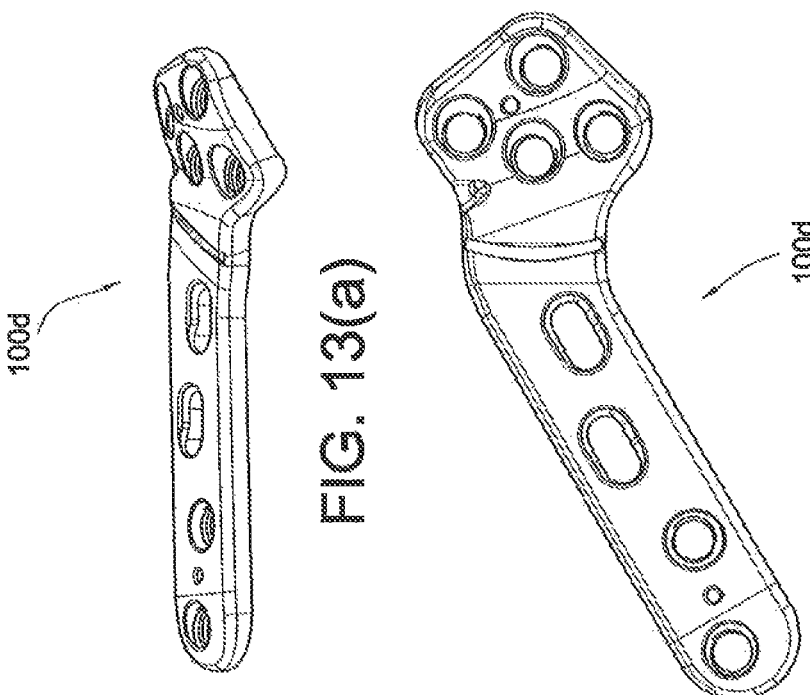

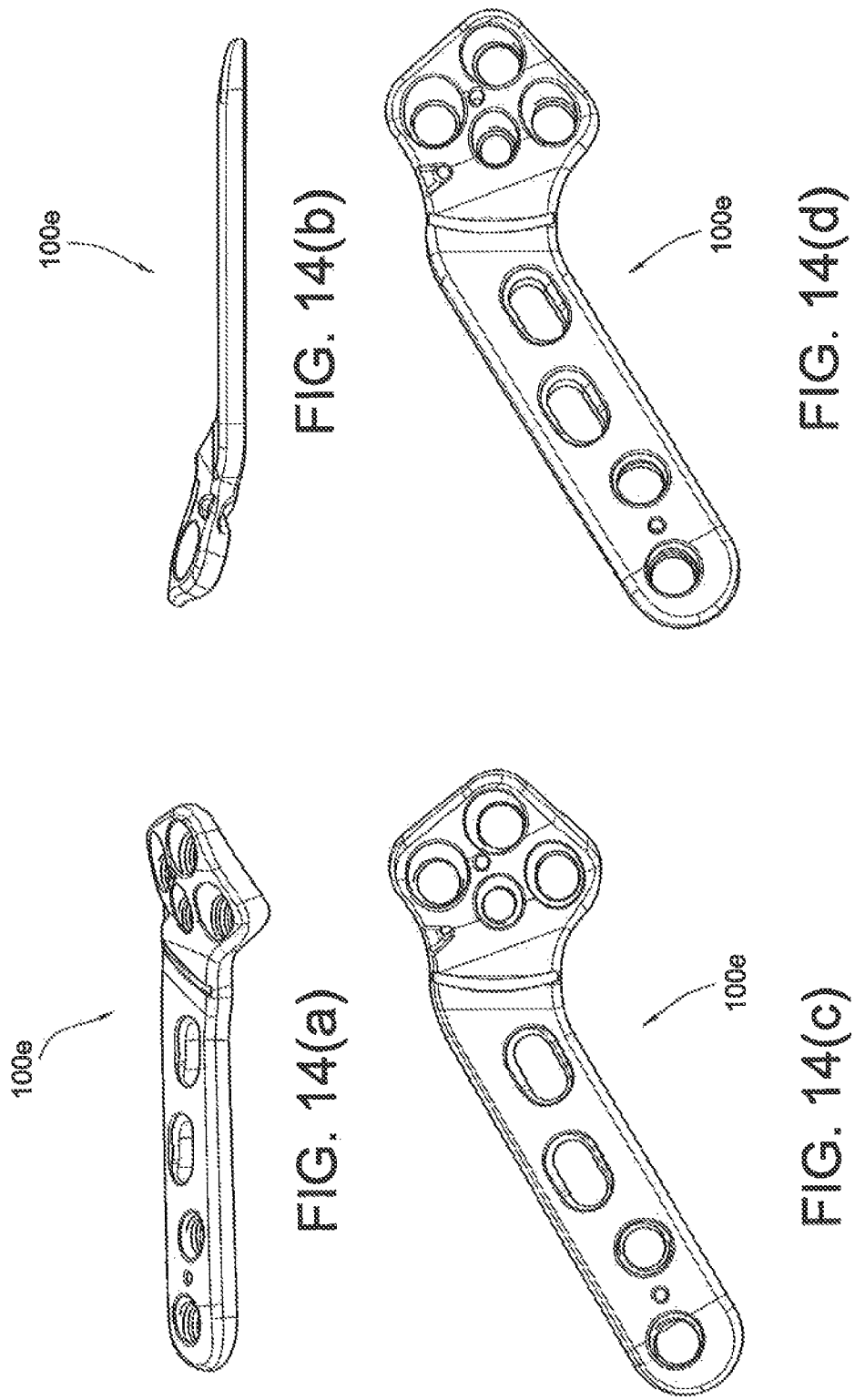

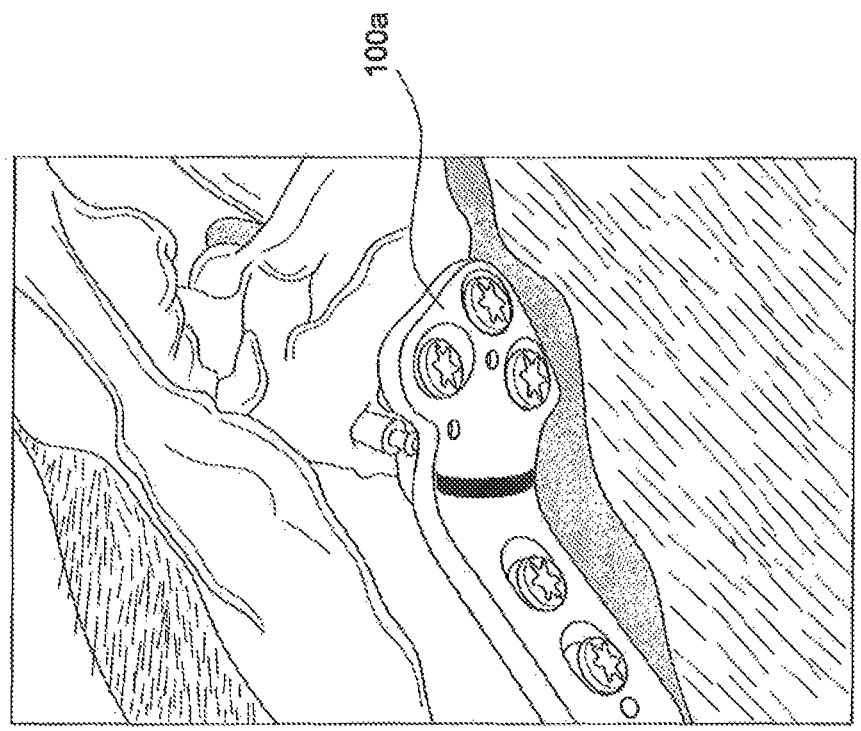
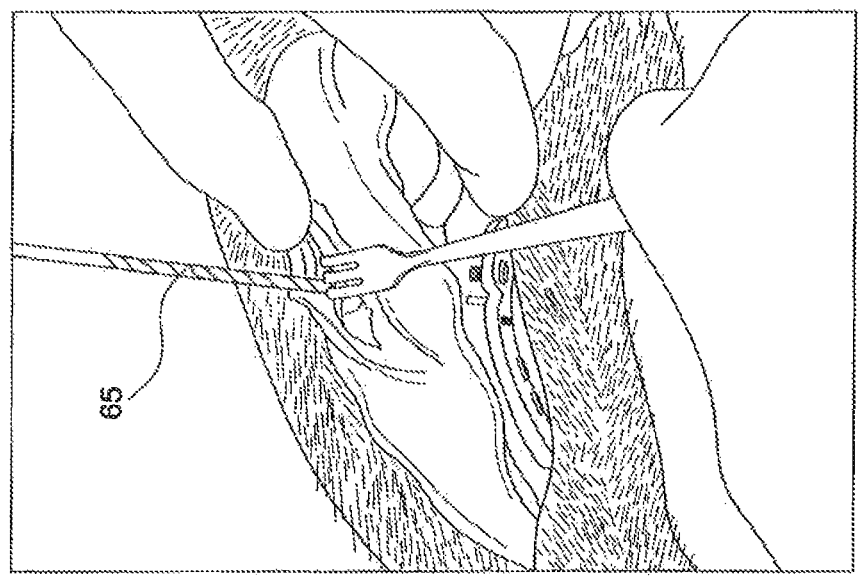
FIG. 23(b)
FIG. 23(a)

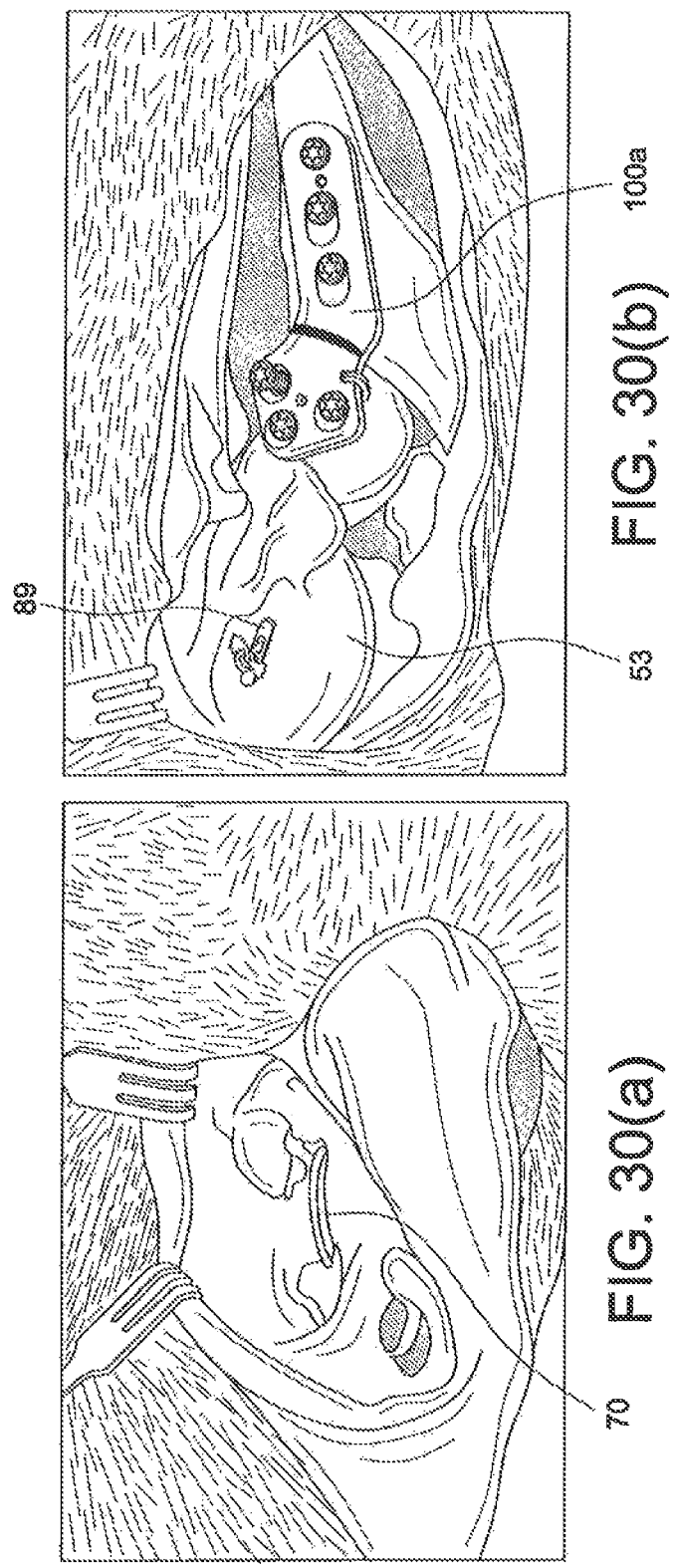

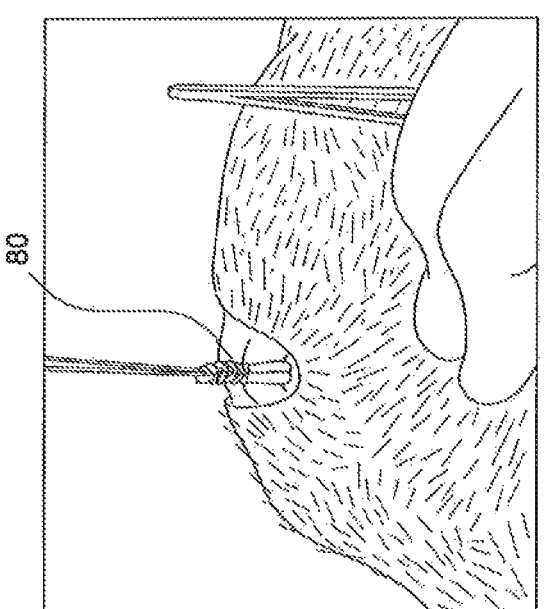
FIG. 31(a)
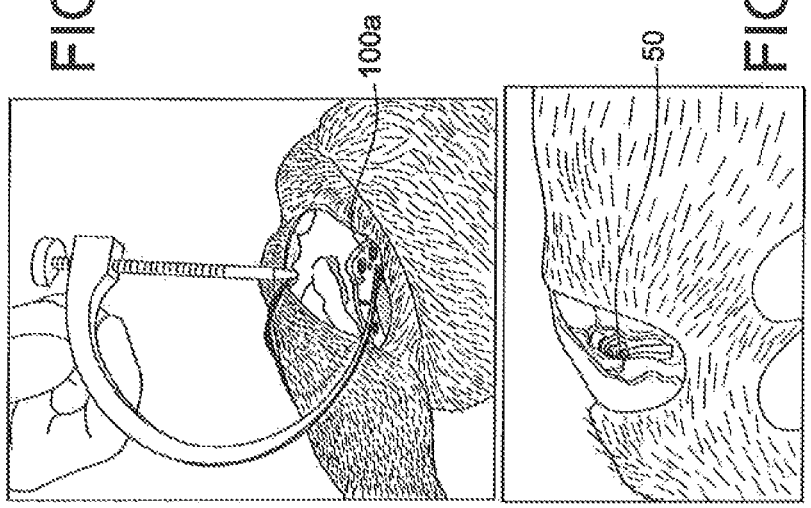
FIG. 31(b)
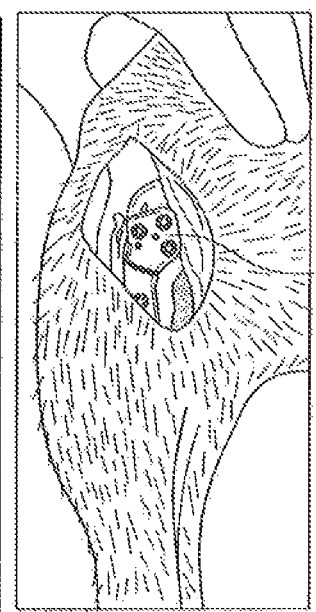
FIG. 31(c)
FIG. 31(d)

TIBIAL PLATEAU LEVELING OSTEOTOMY PLATE

CROSS-REFERENCE TO RELATED APPLICATIONS

This is a continuation of U.S. patent application Ser. No. 16/420,602, filed on May 23, 2019, which is a continuation of U.S. patent application Ser. No. 14/533,768, filed on Nov. 5, 2014, now U.S. Pat. No. 10,299,841, which claims the benefit of U.S. Provisional Application No. 61/900,123, filed on Nov. 5, 2013, the entire disclosures of which are incorporated herein by reference.

FIELD OF THE INVENTION

The present invention relates to methods and apparatus for surgical procedures.

BACKGROUND OF THE INVENTION

Tibial plateau leveling osteotomy (TPLO) procedures are well known in the veterinary art. Tibial plateau leveling osteotomy procedures are used to correct ruptured cranial cruciate ligaments for various animals, particularly canines. These procedures provide an alternative therapy to ligament repair procedures. Tibial plateau leveling osteotomy procedures have become the standard of care for medium and large canines.

When the canine ligament partially or fully ruptures, the tibial plateau leveling osteotomy procedure provides a way to correct this problem. A curvilinear cut is made to the upper portion of the tibia. This cut portion of the tibia is then rotated on the order of about 20-30 degrees to create a more level plane or surface on the top of the tibia upon which the femur can rest. The cut and repositioned portion of the tibia is then secured to the lower portion of the tibia.

There is a need for a TPLO bone plate provided with a new design that allows surgeons to secure to one or more tibial segments of an animal, as part of a tibial leveling osteotomy procedure for an animal. Also needed is a TPLO bone plate that offers a means for providing rotational stability, particularly means for providing additional rotational stability to the TPLO procedure. Also needed is a method of fracture or osteotomy repair in animals that allows securing of dissected soft tissue to the anatomic position where it was dissected, during the fracture or osteotomy repair.

BRIEF SUMMARY OF THE INVENTION

The present invention provides apparatus and methods for bone-tissue fixation (for example, bone-soft tissue fixation) in animals, particularly canines, using a TPLO plate having one or more suture eyelets/holes/slots provided within the body of the plate to allow the user (surgeon) to confer means for providing rotational stability to the joint or the bone, and to the final TPLO repair. The TPLO plate may be also employed, if necessary, to reattach tissue (bone or soft tissue, for example) to the plate at the anatomical location where the tissue was dissected. The suture eyelets/holes/slots may be provided in any number and at any location on the plate, for example, on the proximal region of the plate.

The TPLO plate of the present invention includes a body preferably formed of a metal and one or more suture eyelets (suture holes or slots) or other similar features which are incorporated into the shaft (for example, the proximal region) of the plate. The suture eyelets (holes) may have various shapes, forms and configurations and may be provided on or within a surface of the bone plate in any number, depending on the characteristics of the osteotomy or of the plate design. The suture eyelets preferably receive a flexible strand for fixation of tissue (bone or soft tissue) to the bone plate to improve the rotational stability of the bone or joint.

The present invention also provides a method of improving the rotational stability of a joint or bone, for example, of the knee or stifle during a TPLO procedure. The method comprises the steps of: (i) providing a TPLO plate that includes one or more suture eyelets/holes/openings/slots on or within the bone plate; (ii) fixating the TPLO plate to bone with fasteners such as screws; (iii) passing suture through one or more suture eyelets of the TPLO plate; and (iv) securing the suture to bone to improve the rotational stability of the bone/joint and the overall TPLO repair.

These and other features and advantages of the invention will be more apparent from the following detailed description that is provided in connection with the accompanying drawings and illustrated exemplary embodiments of the invention.

BRIEF DESCRIPTION OF THE DRAWINGS

FIGS. 1-3 illustrate schematic subsequent method steps of a TPLO procedure with an exemplary TPLO bone plate of the present invention.

FIGS. 7-9 illustrate various X-ray views of a TPLO plate of the present invention (superimposed on the TPLO plate of FIGS. 4-6) to illustrate the differences between the TPLO plate of the present invention and the prior art TPLO plate.

FIGS. 11(*a*)-(*d*) illustrate various views of an exemplary 3.5 mm small TPLO plate of the present invention.

FIGS. 13(*a*)-(*d*) illustrate various views of an exemplary 3.5 mm broad TPLO plate of the present invention.

FIGS. 14(*a*)-(*d*) illustrate various views of an exemplary 4.5 mm standard TPLO plate of the present invention.

FIGS. 15-32 illustrate subsequent steps of an exemplary method of TPLO bone plate fixation according to an embodiment of the present invention.

DETAILED DESCRIPTION OF THE INVENTION

Figure 2:
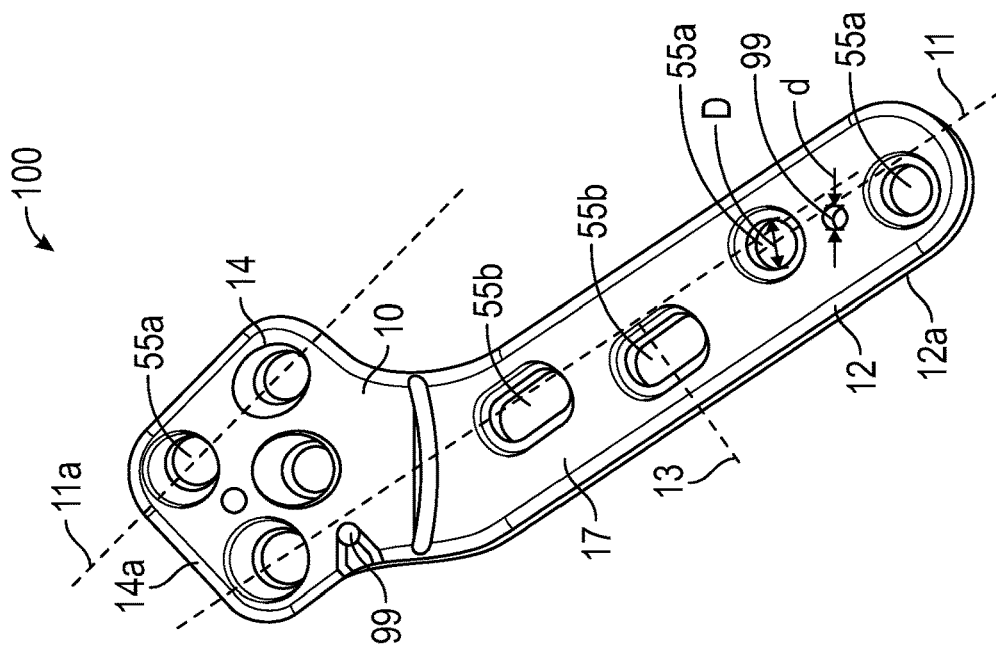

The present invention provides TPLO bone plates having one or more suture eyelets on or within the plate, to allow the user (surgeon) to increase the rotational stability of the bone or joint and, optionally, to reattach the soft tissue to the plate at the anatomical location where the tissue was dissected.

The TPLO bone plates of the present invention are provided in various sizes, for example, 2.7 mm standard, 3.5 mm small, 3.5 mm standard, 3.5 mm broad, 4.5 mm standard, etc., accommodating correspondingly-sized screws. The TPLO bone plates are designed to accept various locking and non-locking low profile cortical screws. In an exemplary embodiment, each plate is provided with a suture hole located cranially on the proximal portion of the plate that accepts one flexible strand, for example a strand of #5 FiberWire® or FiberTape®. Each plate is provided with a surface cut demonstrating where a laser line for the osteotomy will be. All angles and radii for the proximal contour may be equal for each plate design. Some geometries between the 2.7 mm, 3.5 mm, 4.5 mm plates are slightly different.

The TPLO plates of the present invention may be provided as single devices and/or as part of kits incorporating additional instruments and devices. For example, the TPLO plates may be provided with additional components known for TPLO procedures, such as locking and non-locking screws, threaded drill guide, drill guide, graduated drill bit, screwdriver such as hexalobe screwdriver, QuickConnect driver such as hexalobe QuickConnect driver, all sized according to the particular dimensions of the TPLO plate to be employed with.

The present invention also provides a TPLO procedure that improves the rotational stability of the joint or bone. The method comprises the steps of: (i) providing a TPLO plate that includes one or more suture eyelets/holes/openings/slots/apertures on or within the bone plate; (ii) fixating the TPLO plate to bone with fasteners such as screws; (iii) passing suture through one or more suture eyelets of the TPLO plate; and (iv) tying the suture to bone to improve the rotational stability of the joint or bone.

An exemplary method of fixation of anatomical tissue during surgical applications by employing a TPLO plate that improves the rotational stability of the bone or joint or repair site (surgical site), and also allows reattachment of soft tissue to bone and to the plate, comprises the steps of: (i) providing a TPLO plate that includes one or more suture eyelets/holes/openings/slots/apertures on or within the bone plate; (ii) placing the TPLO plate on the bone and dissecting the adjacent soft tissue to allow the plate to fit; (iii) fixating the TPLO plate to bone with fasteners such as screws; (iv) passing suture around the bone and through the suture eyelets of the TPLO plate; (v) passing suture through the dissected soft tissue and through the suture eyelets of the TPLO plate; and (vi) tying the suture to improve the rotational stability of the bone/joint/repair site, and to secure the dissected soft tissue to the anatomical position/location where it was dissected.

Figure 1:
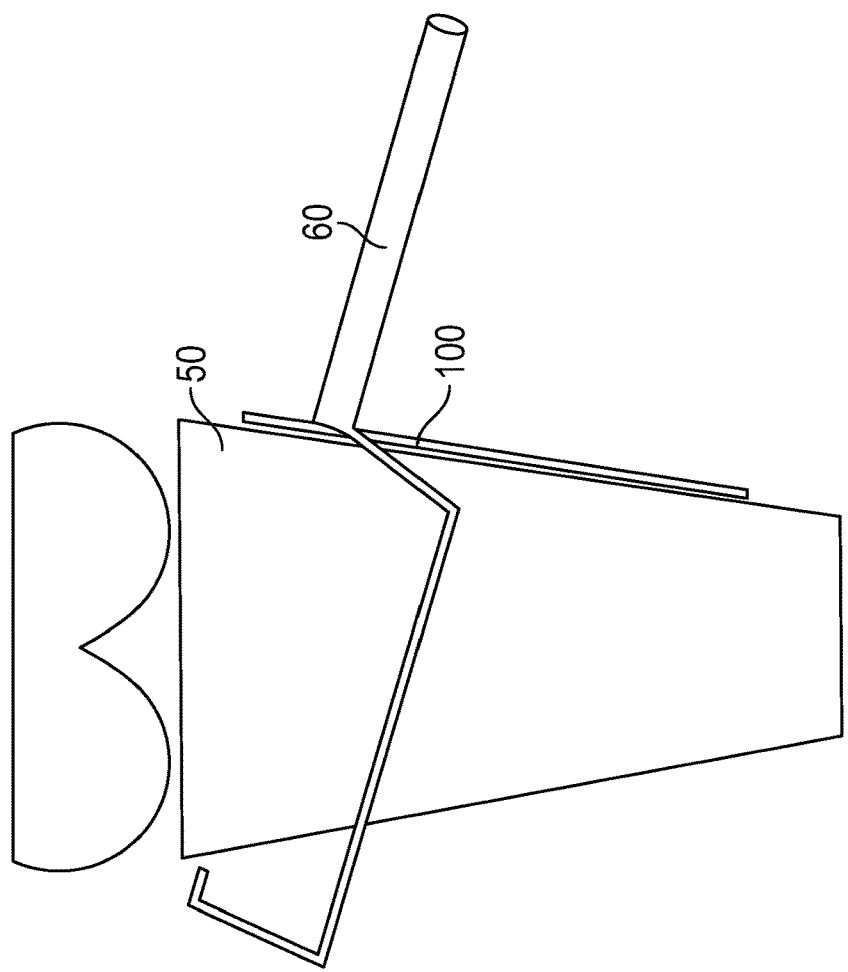

Referring now to the drawings, where like elements are designated by like reference numerals, FIGS. 1-3 illustrate a TPLO plate 100 of the present invention provided with a plurality of suture eyelets 99 (openings/slots/holes/apertures 99) incorporated into the plate to allow soft tissue attachment to the plate. For exemplary purposes only, the TPLO plate 100 is illustrated and described below as a bone plate for providing improved rotational stability in osteotomies of an animal such as a canine, and attachment of dissected biceps and/or adjacent muscles. However, the invention has applicability to the fixation of other bones or bone segments of canines or of other animals, including the fixation of associated soft tissue to bones or bone segments.

As shown in FIG. 2, the TPLO plate 100 includes a rigid body 10 with a longitudinal axis 11, a transversal axis 13, a first surface 17 and a second bone-contacting surface 19. Body 10 is preferably formed of a metal such as titanium, titanium alloy, stainless steel, or other materials that possess mechanical and physical properties suitable for coupling bones together. Body 10 is also defined by a distal region 12 (shaft 12) surrounded by a distal edge 12a and a proximal region 14 surrounded by a proximal edge 14a.

The body 10 of the TPLO plate 100 is provided with a first plurality of through holes or openings 55a, 55b that receive corresponding screws or similar fixation devices 25 to secure the bone plate to bone. The fixation devices 25 may be screws, anchors, washers or any combination thereof for securing the bone plate to bone. The first plurality of openings 55a, 55b extend from the first surface 17 through the body 10 and to the bone-contacting surface 19, for accommodating at least one fixation device. Openings 55a, 55b may be provided in any number and may have similar or different perimeters. Openings 55a, 55b may be also optimally placed in the body 10 of the plate and at various angles with respect to transversal axis 13 of the plate 100. Additional small holes may be added within the body of the plate for the purpose of inserting k-wires to help keep the plate stable during the process of fixating the plate to the bone. Exemplary plate designs may incorporate a single suture hole with a diameter approximately double than that of the diameter of k-wire holes.

The first plurality of openings 55a, 55b includes a first set of holes 55a located within the proximal region 14 and the distal region 12 and extending asymmetrically along the longitudinal axis 11 of the body 10, and a second set of holes 55b located only within the distal region 12 and in asymmetry relative to the longitudinal axis 11 of the body 10.

At least one of the openings 55a may include spherical bushings to allow variable angle-locking to be achieved by threading at least one tapered locking screw into the spherical bushings, as detailed below. The tapered head will expand the bushing, locking the screw to the plate. Non-locking screws may be also employed and can be placed in any opening 55a. If polyaxial bushings is employed, the polyaxial bushings offer the surgeon the freedom to direct the fixation devices (for example, screws) within the anatomical template, based on the fracture pattern and bone quality for better fixation and to achieve a low profile polyaxial suture plate with any angulation, for example, a 60 degree angulation. The polyaxial bushings in each hole provide multi-directional locking or non-locking capability of the plate/screw construct to the bone. Drill guides can angulate the bushing to the desired screw trajectory.

Openings 55a may be provided in any number and may have similar or different perimeters. In the exemplary embodiment shown in FIG. 2, openings 55a are circular and have the same diameter, while openings 55b are oval and have same shape and dimensions. Openings 55a, 55b may be also optimally placed in the body 10 of the bone plate and at various angles with respect to a transversal axis of the TPLO plate 100. Openings 55a, 55b are preferably arranged non-linearly with respect to the longitudinal axis 11, for the 3.5 mm broad plates and 4.5 standard plates. In addition, as and shown in FIG. 2, axis 11a passing through both centers of openings 55a located on proximal region 14 and disposed along edge 14a is about parallel to the longitudinal axis 11 of the body of the plate 100.

As also shown in FIGS. 1-3, the TPLO plate 100 includes a second plurality of through holes or apertures including one or more suture eyelets 99 (suture holes or slots) which are disposed within the body 10 of the bone plate 100. Exemplary TPLO plate 100 includes one, two or three suture eyelets or holes 99.

The suture eyelets 99 preferably receive a flexible strand 70 (FIG. 3) to increase the rotational stability of the bone or joint. The suture eyelets may also help in the fixation of soft tissue 80 to the bone plate 100. For example, and if desired, suture eyelets 99 allow the user (surgeon) to reattach soft tissue 80 to the plate at the anatomical location where the tissue was dissected. The suture eyelets 99 may have various shapes, forms and configurations and may be provided on or within a surface of the bone plate 100 in any number, depending on the characteristics of the osteotomy or of the plate design.

Suture eyelets 99 may be recessed and they extend from the first surface 17 through the body 10 and to the bone-contacting surface 19, to accommodate at least one flexible strand attached to soft tissue to be reattached to the bone and to increase the rotational stability of the bone or joint. Although reference to the eyelets 99 will be made below as to the suture eyelets 99, the invention is not limited to this exemplary-only embodiment and contemplates eyelets for passing of any flexible strand, for example, suture, suture tape such as FiberTape®, suture chain such as FiberChain®, or a flexible material forming (or part of) a continuous loop/button construct provided with a button and a continuous loop attached to the button, among many others.

Suture eyelets 99 may be chamfered suture eyelets or provided with fillets. Suture eyelets 99 are provided within the body of the plate 100 to allow the user (surgeon) to pass one or more flexible strands (for example, one or more suture strands such as FiberWire® suture) after or before the plate is fixed to bone. In this manner, suture eyelets 99 allow the user (surgeon) to reattach soft tissue 80 to the plate at the anatomical location where the tissue was dissected and to also increase the rotational stability of the bone or joint. The suture eyelets 99 (holes/apertures/openings or chamfered suture eyelets 99) may have various shapes, forms and configurations and may be provided on or within a surface of the TPLO plate 100 in any number. The suture eyelets 99 preferably receive at least one flexible strand 70 for fixation of soft tissue 80 to the TPLO plate 100. One or more flexible strands may be passed through one suture eyelet. One flexible strand may be passed through one or more suture eyelets.

In an exemplary embodiment, the first plurality of openings 55a have a first uniform diameter "D" (FIG. 2) and the second plurality of suture eyelets 99 have a second uniform diameter "d" (FIG. 2) which is smaller than the first diameter "D." The first diameter "D" is preferably at least four times larger than the second diameter "d."

According to another exemplary embodiment, the bone plate 100 of the present invention has one suture eyelet and two other small holes that are intended for passing k-wires or similar instruments to facilitate stability of the plate prior to fixation with screws. The holes of the plate for accommodating fixation devices (screws) preferably are provided asymmetrically relative to the longitudinal axis of the body of the plate. Other embodiments may also have only one oval hole or two oval holes that are centered on the longitudinal axis of the body of the plate.

The present invention also provides a suture plate kit (assembly) with a bone plate 100 (suture plate 100) of the present invention and a suturing kit including at least one flexible strand attached to at least one needle. The at least one flexible strand may be FiberWire® suture containing color coded suture, for example, a #2 and/or #5 FiberWire® sutures, with needles on each end, to facilitate suturing the soft tissue to the bone plate after the plate is in place. The needles may be attached to the suture by any method known in the art, for example, by being swedged onto the suture. FIG. 3 illustrates exemplary TPLO bone plate 100 of the present invention with tissue 80 to be attached to its proximal region 14 and with attached suture 70 to be passed through one of the suture eyelets 99 (the cranial proximal eyelet 99) for further attachment of soft tissue to TPLO plate 100.

The present invention also provides a method of forming a TPLO plate having suture holes for soft tissue attachment (or reattachment) for surgical application and for increasing the rotational stability of the joint or the bone. One to three suture eyelets 99 are formed within the body of a TPLO plate to enable a surgeon to easily place the tissue 80 to be attached/reattached back to the bone (for example, ligament or other soft tissue) during a TPLO procedure.

The present invention also provides a method of stabilizing a canine proximal tibia, comprising inter alia the steps of: (i) providing a TPLO plate having a body with a first surface, a second surface opposed to the first surface, the body having a proximal region and a distal region, a first plurality of apertures passing through the plate, the first plurality of apertures accommodating a plurality of fixation devices, a second plurality of apertures passing through the plate, the second plurality of apertures accommodating a plurality of flexible strands attached to soft tissue to be reattached to the bone; (ii) securing the TPLO plate to tibia by inserting the plurality of fixation devices at various angles relative to a transversal axis of the body; (iii) passing at least one flexible strand (for example, monofilament suture) through at least one of the second plurality of apertures; and (iv) securing the at least one flexible strand to femur or to soft tissue with a fixation point on the femur, to improve the rotation stability of canine bone or joint.

FIGS. 1-3 illustrate exemplary steps of a TPLO procedure with TPLO plate 100 of the present invention for repair of bone segments of tibia 50 (at a tibia-femur joint region in the leg of an exemplary canine).

FIG. 1: Use a current C-guide 60 or similar instrument to allow driving suture passing pin 66 (FIG. 3) through plate holes to desired tibial tunnel entrance.

FIG. 2: The TPLO plate 100 has two or three exemplary suture holes/slots 99 at a location where they would work. Could also have just one or button recess, depending on the characteristics of the particular repair.

FIG. 3: Prepare biceps tendon 80 for transposition for bio-extracap; pull end of suture 70 (one at a time through, to tie over the TPLO plate 100). Could also repeat procedure with fabellar suture, anchor, or suture loop/fixation device (for example, a TightRope® device), as detailed below. This procedure would also eliminate the need to extend the incision or struggle to reach to the lateral femoral area.

FIGS. 4-9 illustrate various views of the shape and position holes of a prior art plate 1 and of an exemplary TPLO plate 100' of the present invention.

Figure 5:
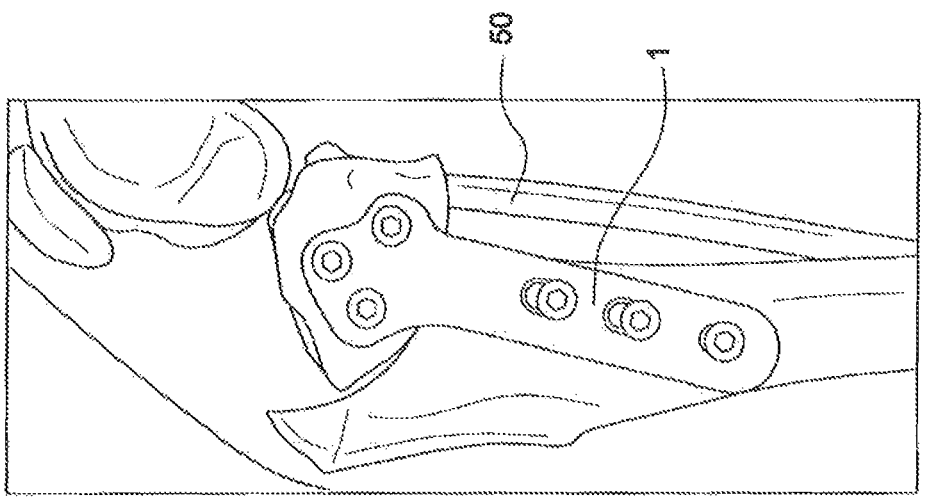
Figure 4:
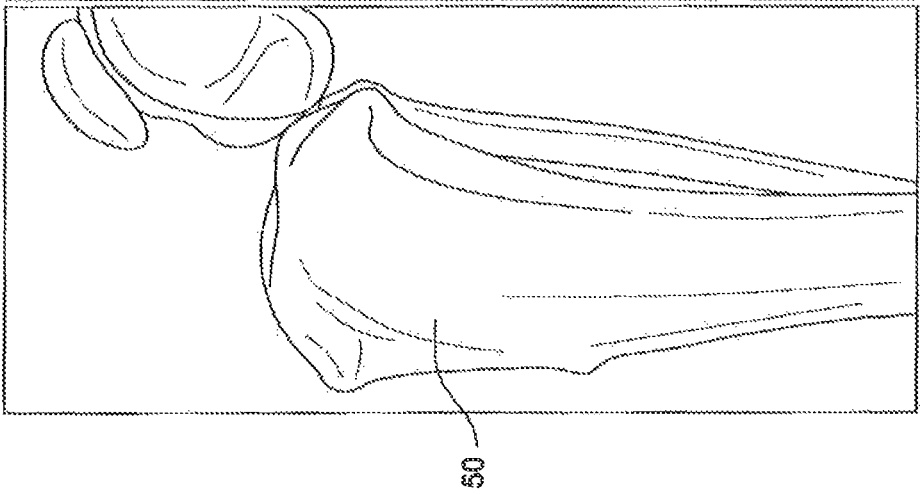
Figure 10A:
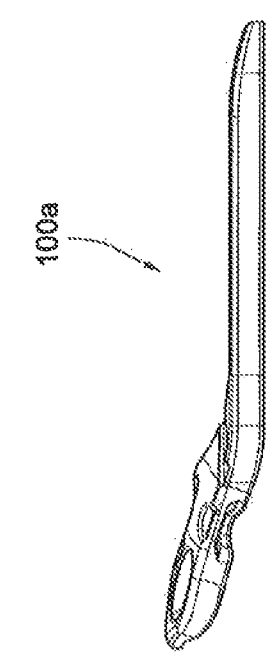
FIGS. 10(*a*)-(*d*) illustrate various views of an exemplary 2.7 mm standard TPLO plate of the present invention.
Figure 10B:
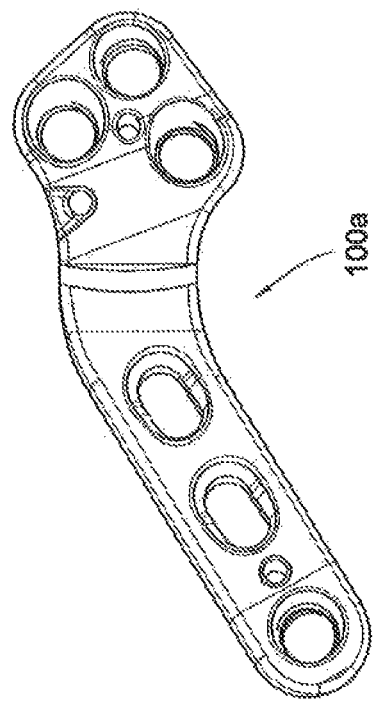
Figure 10C:
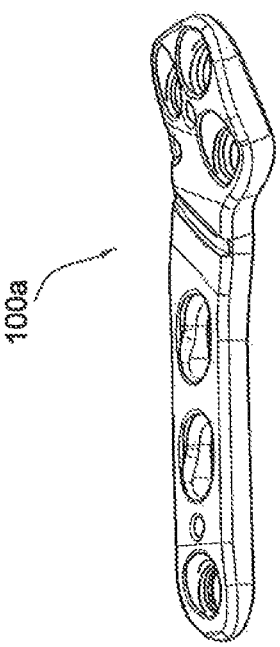
Figure 10D:
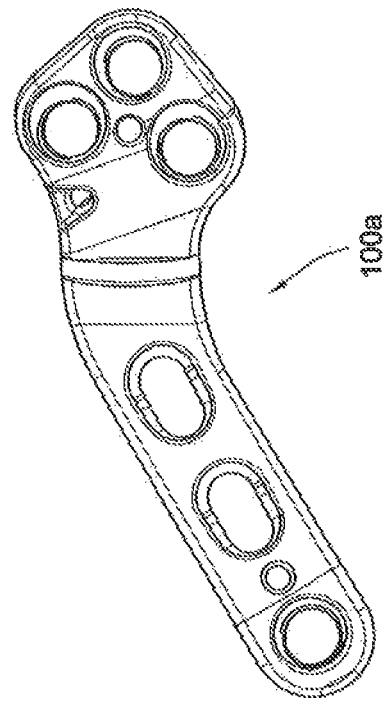
Figure 12A:
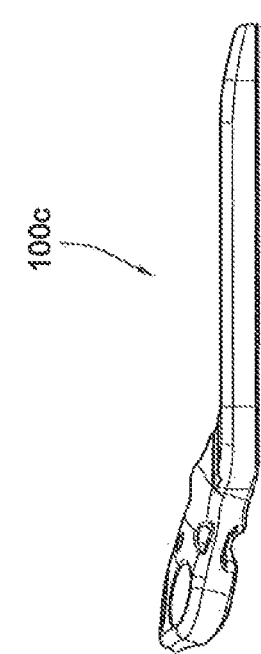
FIGS. 12(*a*)-(*d*) illustrate various views of an exemplary 3.5 mm standard TPLO plate of the present invention.
Figure 12B:
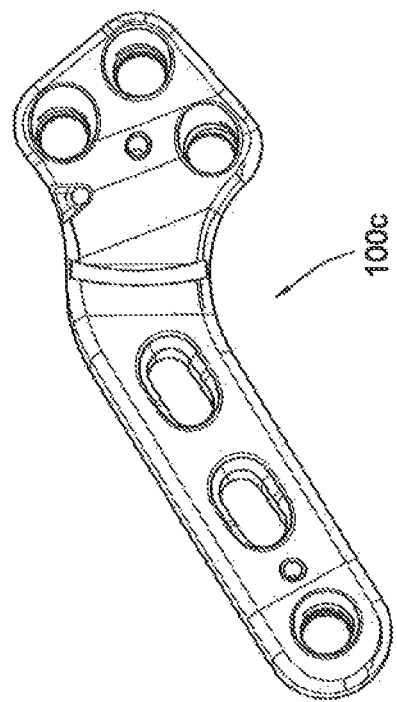
Figure 12C:
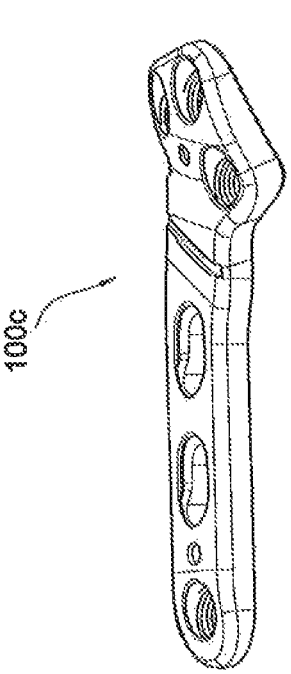
Figure 12D:
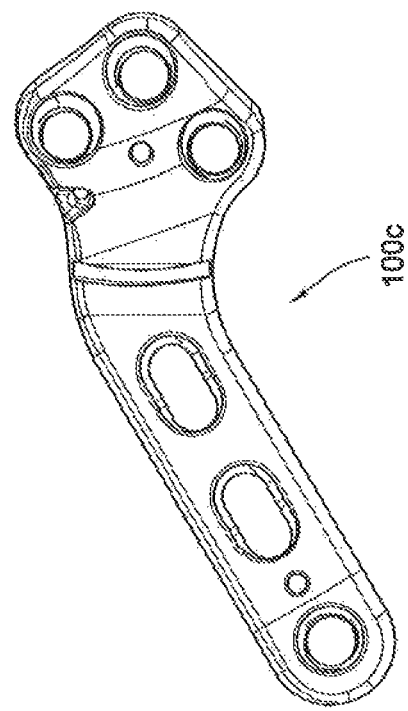

FIG. 5: plate 1 is tilted to position; proximal screws are located in the middle of the fragment.

Figure 6:
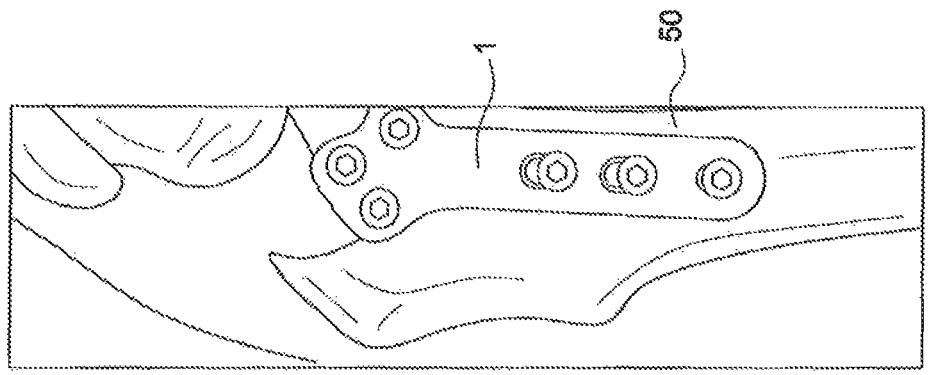
FIGS. 4-6 illustrate various X-ray views of a TPLO plate of the prior art positioned on canine tibia.

FIG. 6: plate 1 is straight but the screws are too close with the osteotomy cranially.

FIG. 7: illustrates exemplary TPLO plate 100' of the present invention superimposed with plate 1 of the prior art.

FIG. 8: illustrates TPLO plate 100' of FIG. 7 with an exemplary eyelet 99a located at a first position on the proximal region of the body of the plate (Option 1).

FIG. 9: illustrates TPLO plate 100' of FIG. 7 with another exemplary eyelet 99b located at a second position on the proximal region of the body of the plate (Option 2).

FIGS. 10(*a*)-(*d*) illustrate various views of an exemplary 2.7 mm standard TPLO plate 100a of the present invention. FIGS. 11(*a*)-(*d*) illustrate various views of an exemplary 3.5 mm small TPLO plate 100b of the present invention. FIGS. 12(*a*)-(*d*) illustrate various views of an exemplary 3.5 mm standard TPLO plate 100c of the present invention. FIGS. 13(*a*)-(*d*) illustrate various views of an exemplary 3.5 mm broad TPLO plate 100d of the present invention. FIGS.

14(a)-(d) illustrate various views of an exemplary 4.5 mm standard TPLO plate 100e of the present invention.

Reference is now made to FIGS. 15-32 which illustrate subsequent steps of a method of TPLO bone plate fixation according to an embodiment of the present invention and employing an exemplary TPLO plate 100, 100a, 100b, 100c, 100d, 100e, 100' of the present invention.

Figure 15:
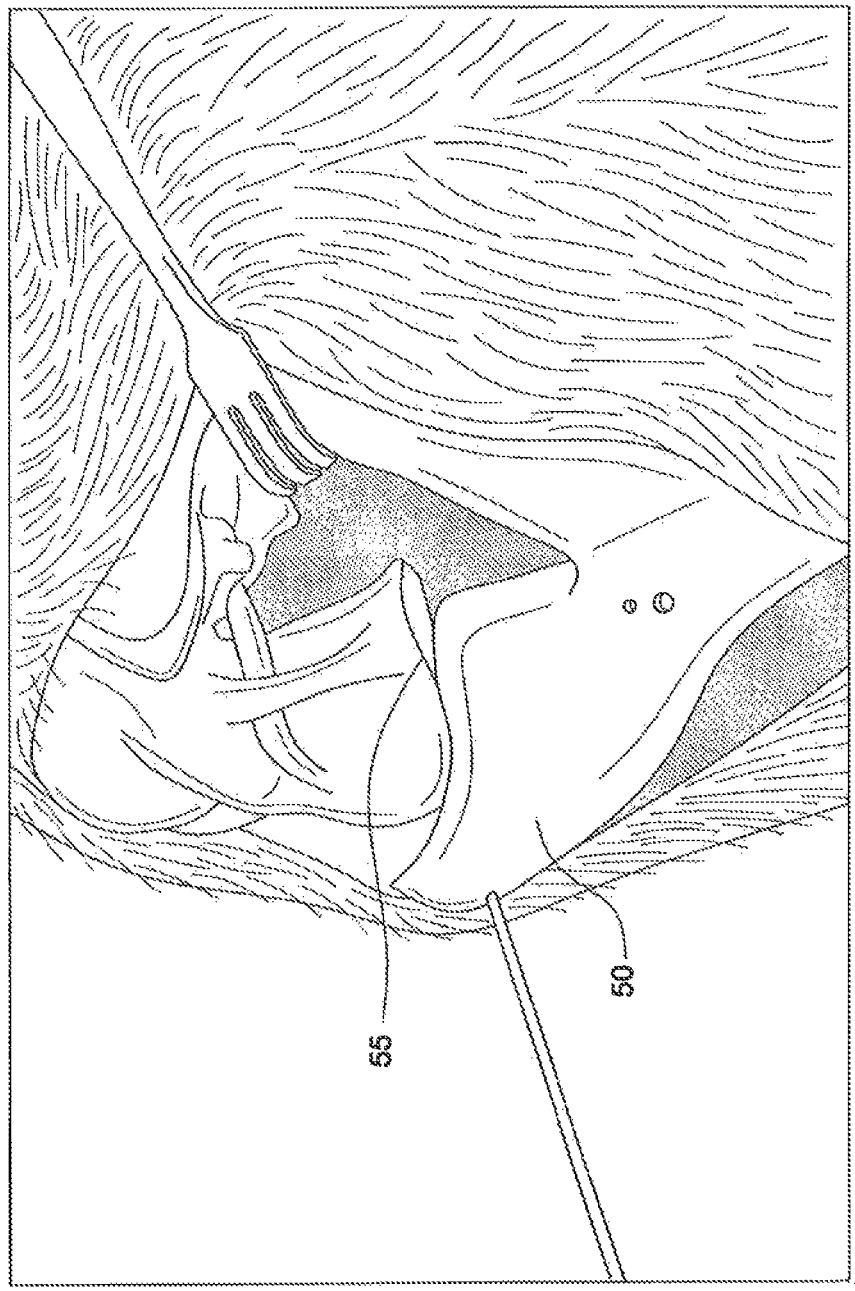
Figure 16:
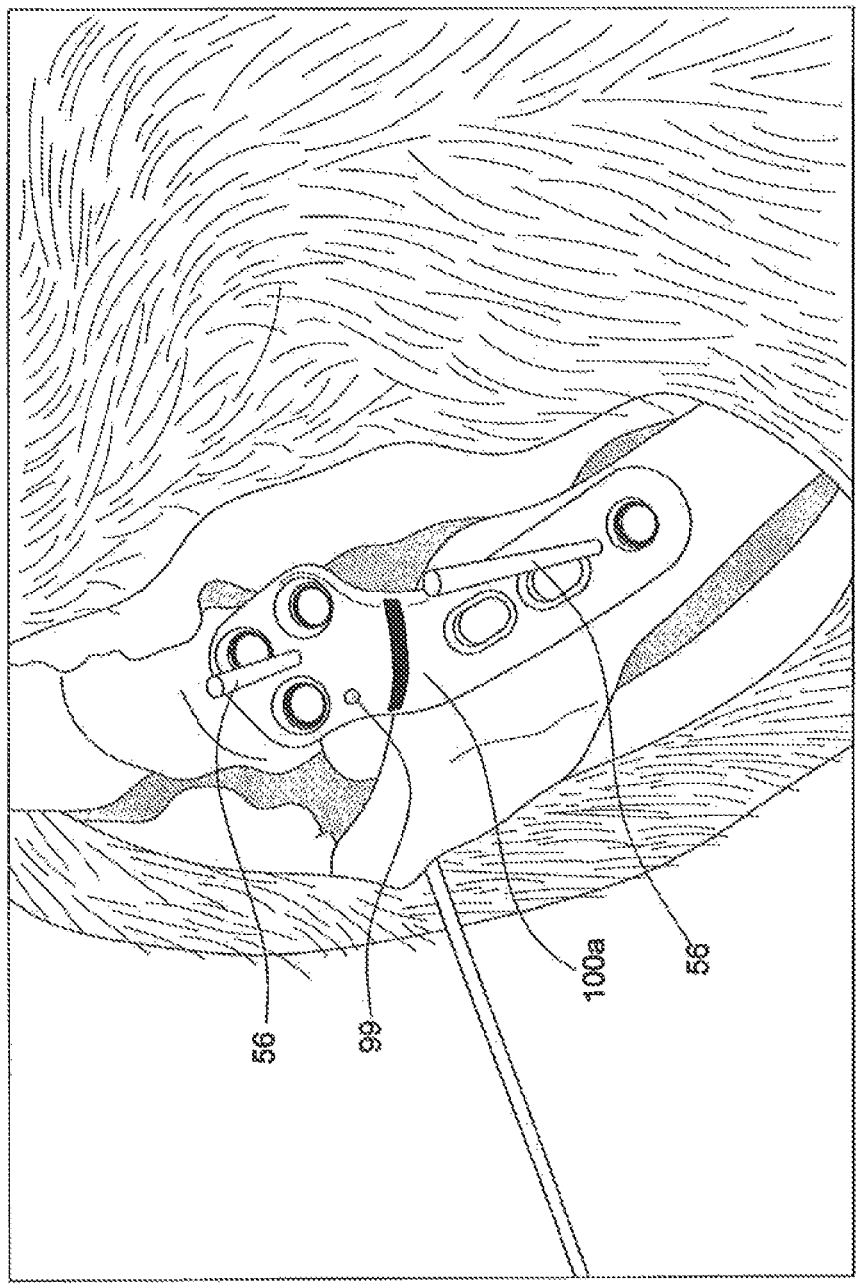
Figure 17:
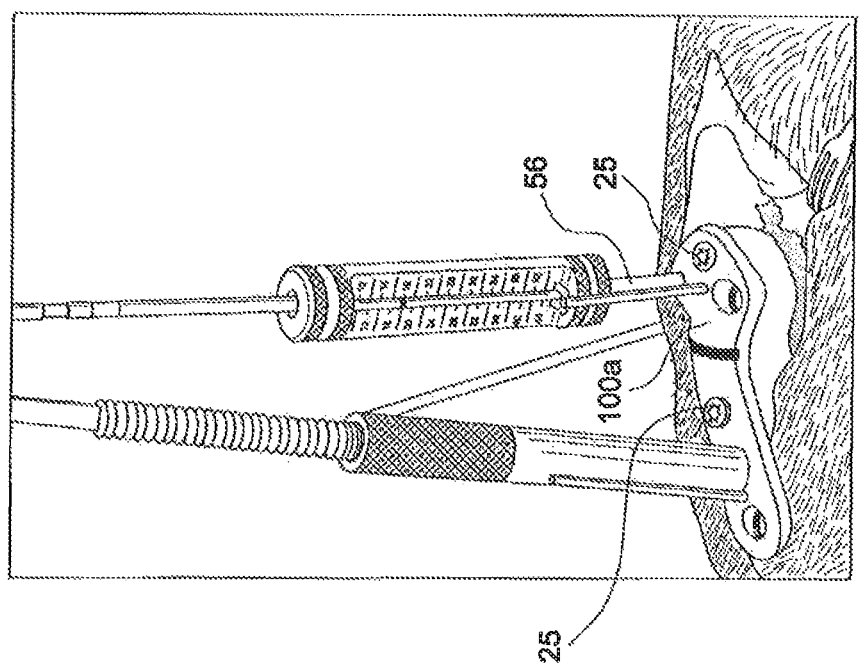
Figure 18:
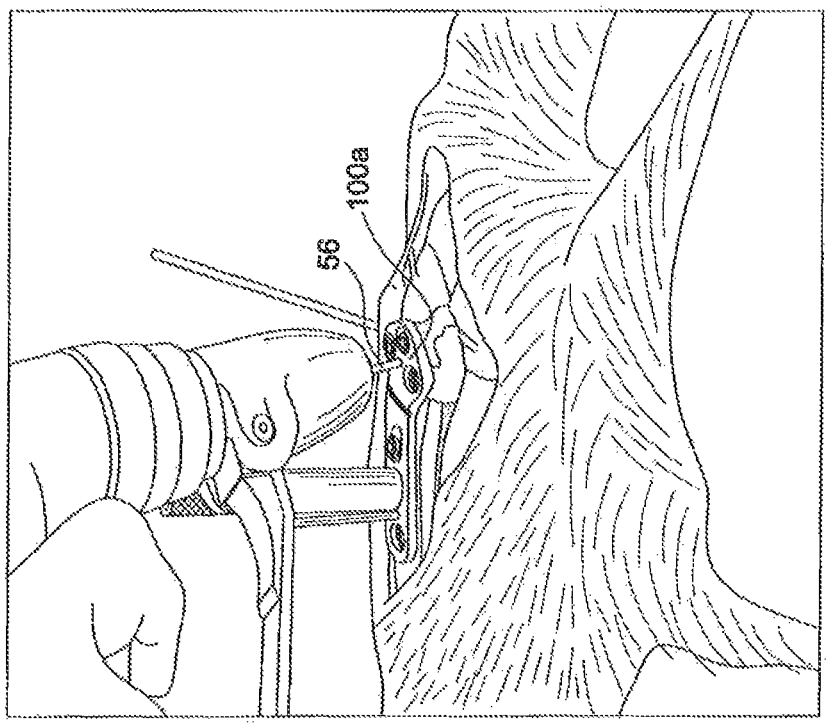
Figure 19:
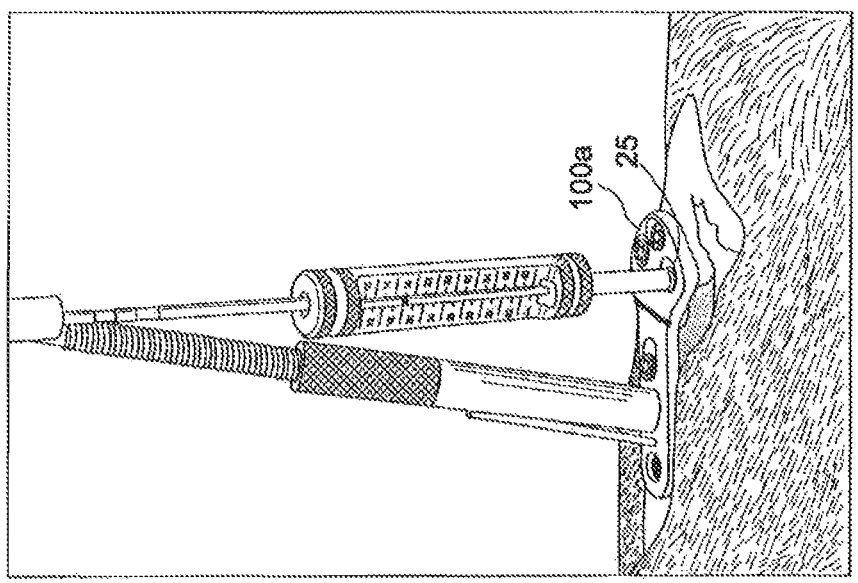
Figure 20:
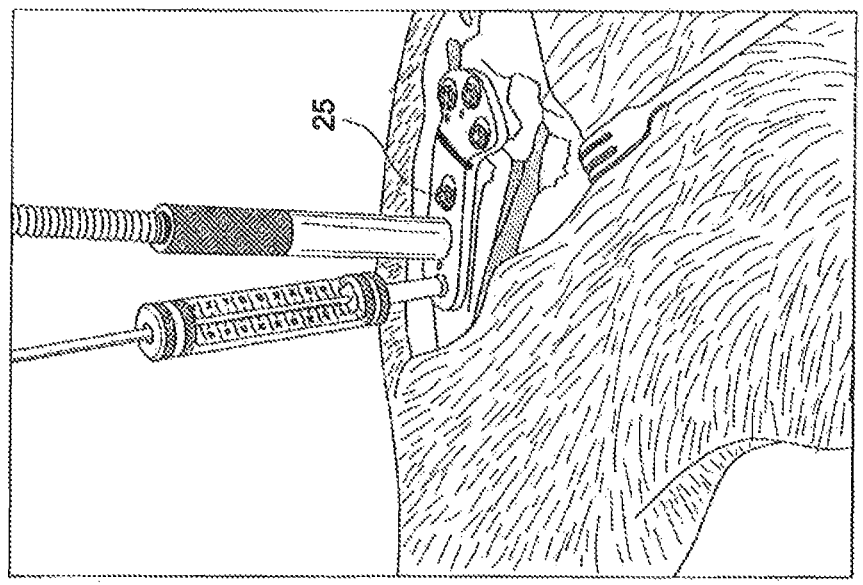
Figure 21:
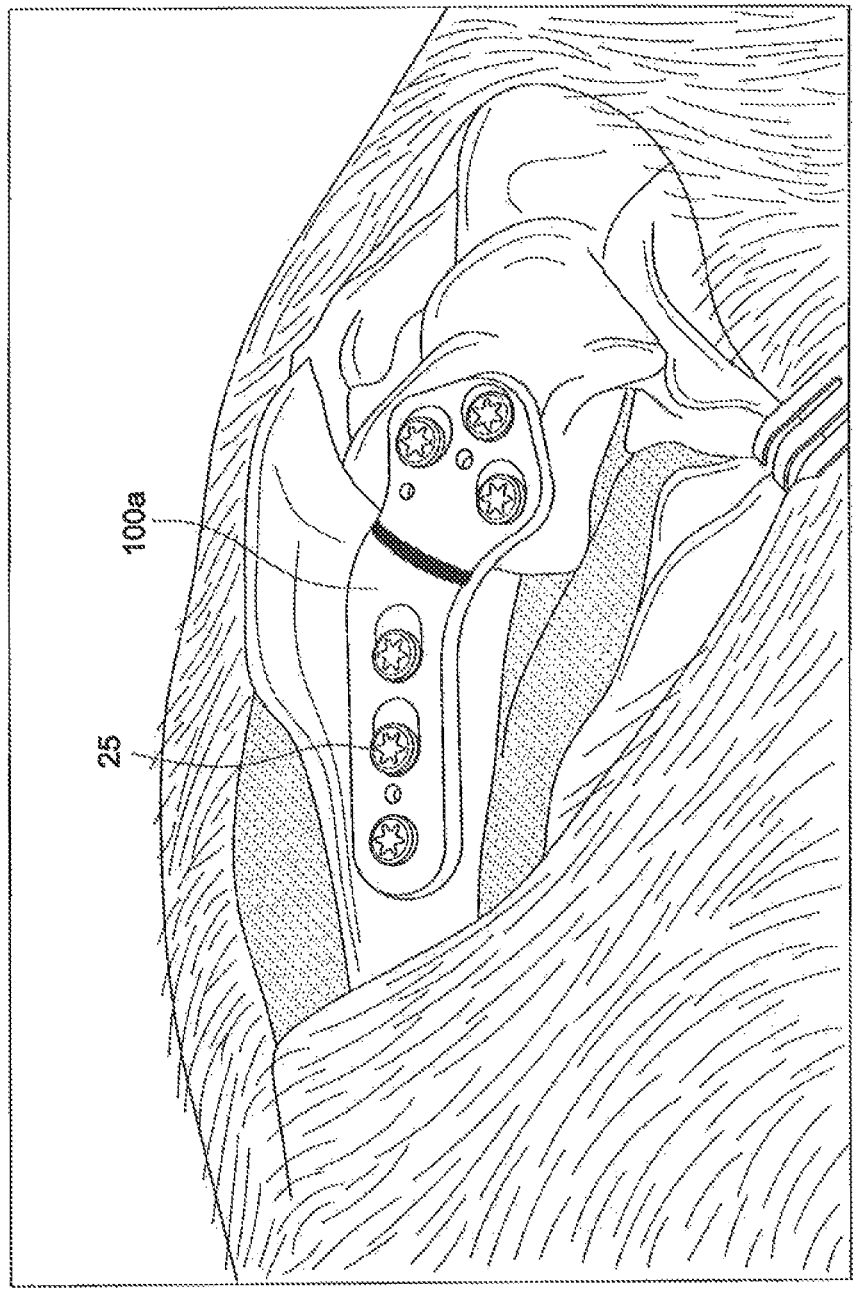

The method begins by fixating exemplary TPLO plate 100a by employing known fixation steps in the art and as listed below:

Create and pin the osteotomy 55 at the level of tibia 50 (FIG. 15);
Check the TPLO plate 100a first;
Position TPLO plate 100a using K-wires 56 (for example, 0.062" K-wires 56) (FIG. 16);
Fixate TPLO plate using a fixation instrument (for example, a push-pull device, or a clamp/plier type device to fixate the plate);
Drill in loaded position of compression slot (for example, proximal compression slot);
Check screw depth;
Insert non-locking screw partially;
Drill proximal holes 15 and insert screws 25 (FIG. 17);
Remove proximal positioning K-wire 56 (FIG. 18);
Remove osteotomy K-wire;
Drill and insert final proximal screw 25 (FIG. 19);
Remove distal K-wire;
Fully insert compression screw;
Drill and insert distal locking screw 25 (FIG. 20);
Remove fixation instrument (for example, push-pull device, or clamp/plier type device);
Drill and insert screw in compression slot (for example, distal compression slot) (FIG. 21).

Figure 22:
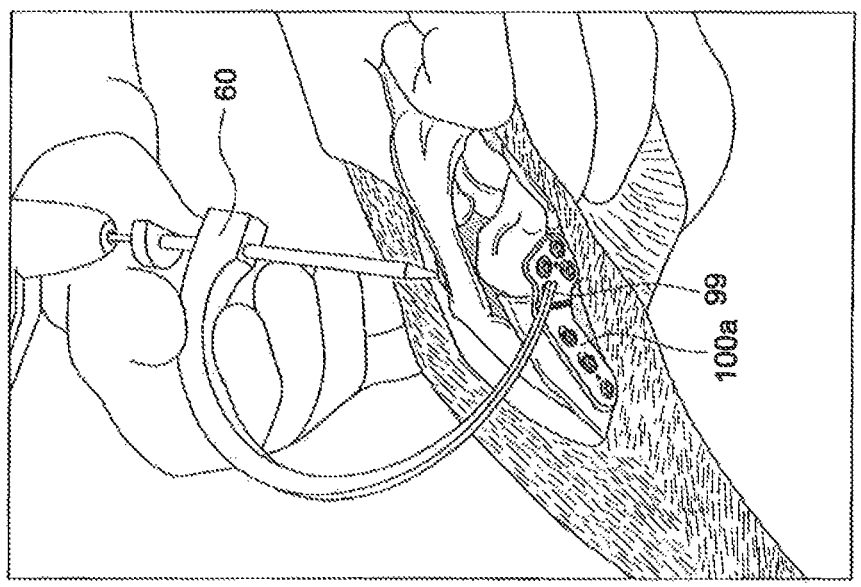
Figure 24:
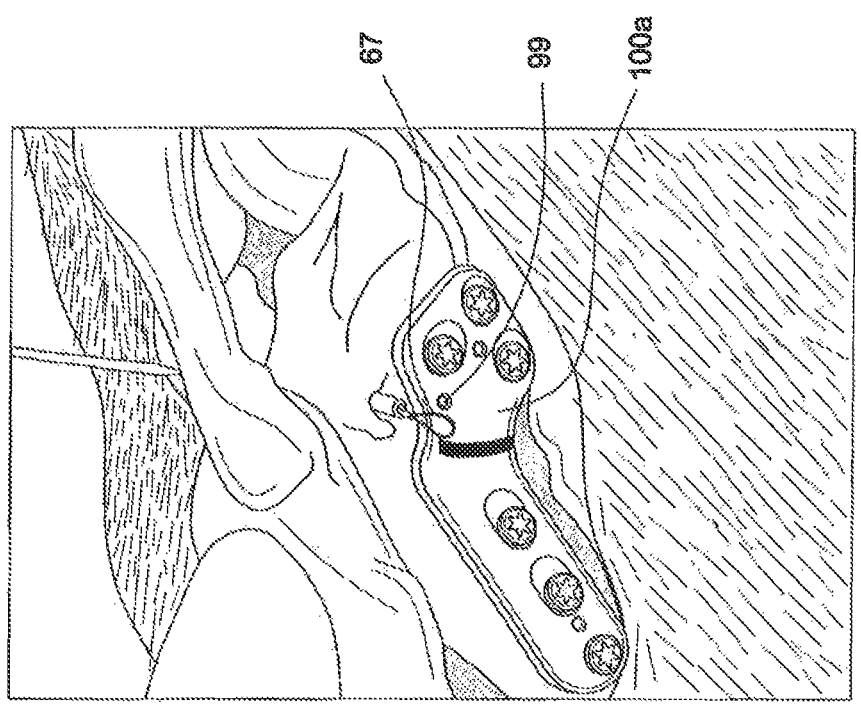
Figure 25:
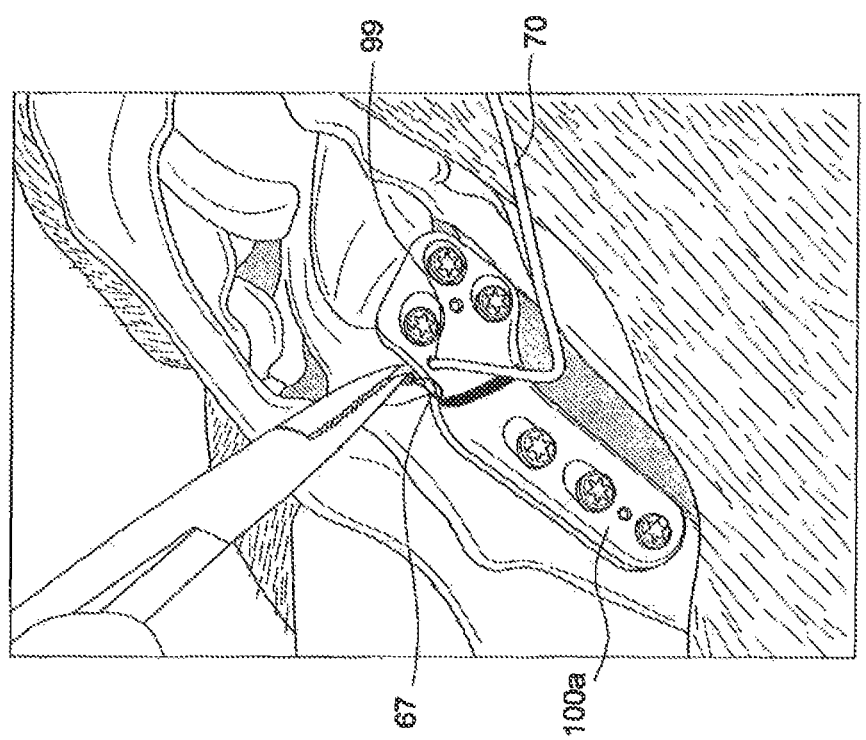
Figure 26:
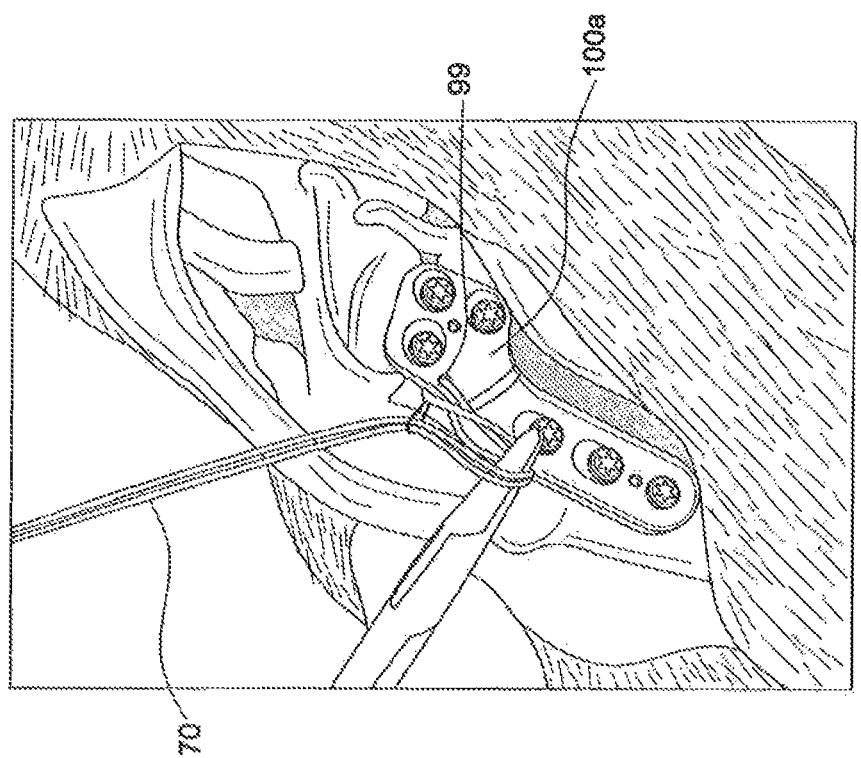
Figure 27:
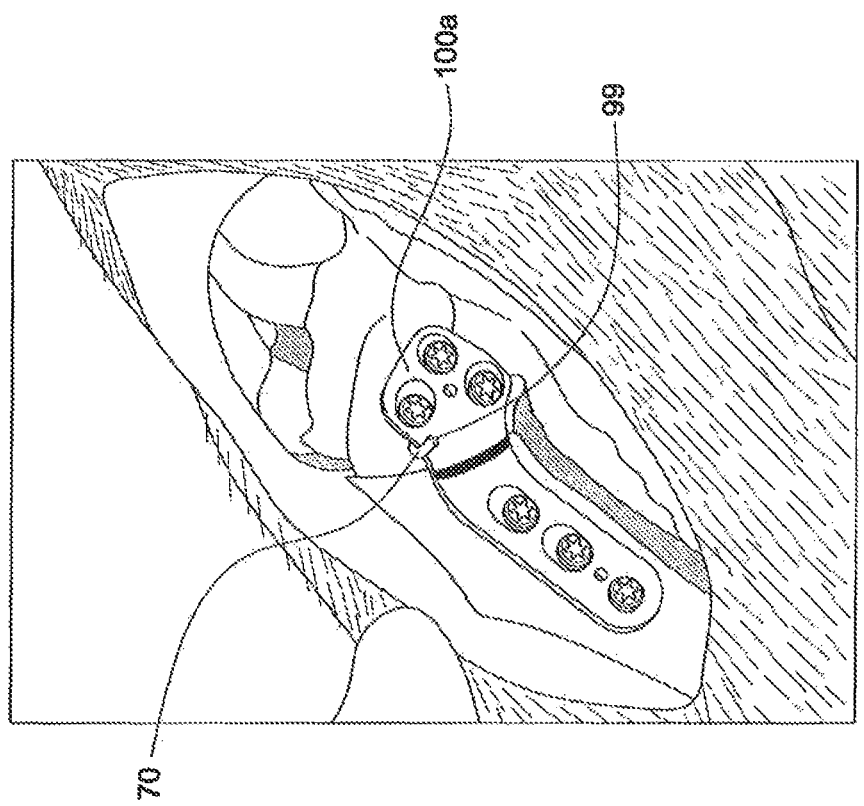
Figure 28B:
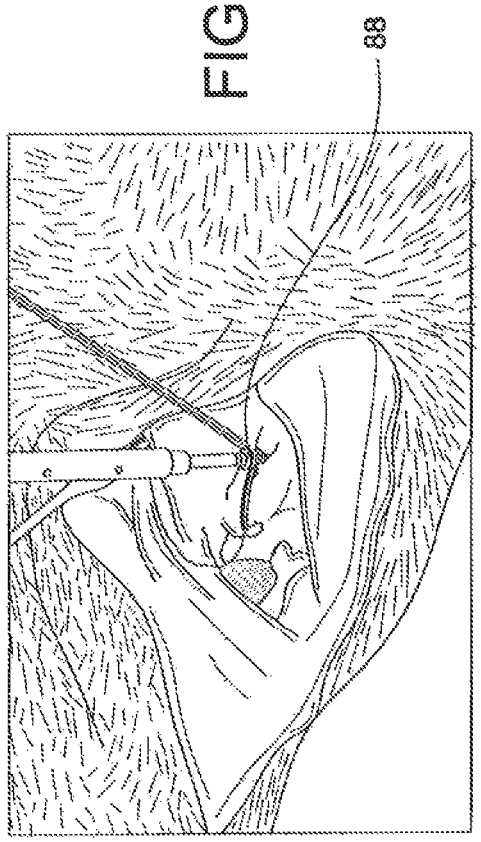
Figure 28C:
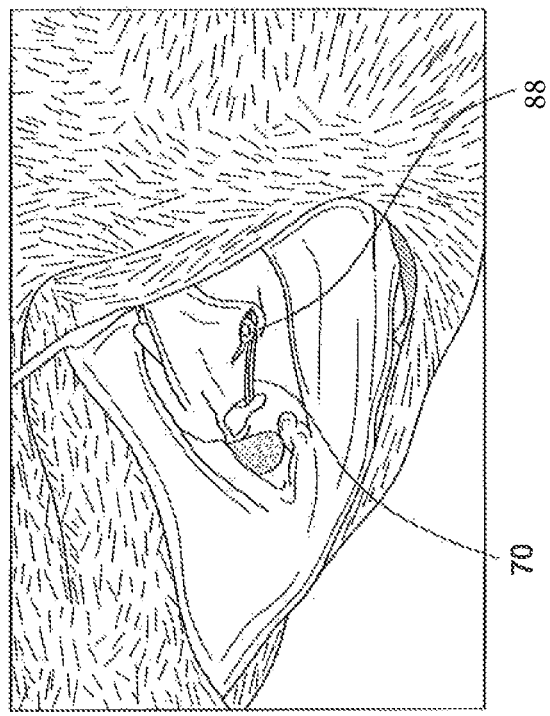
Figure 28A:
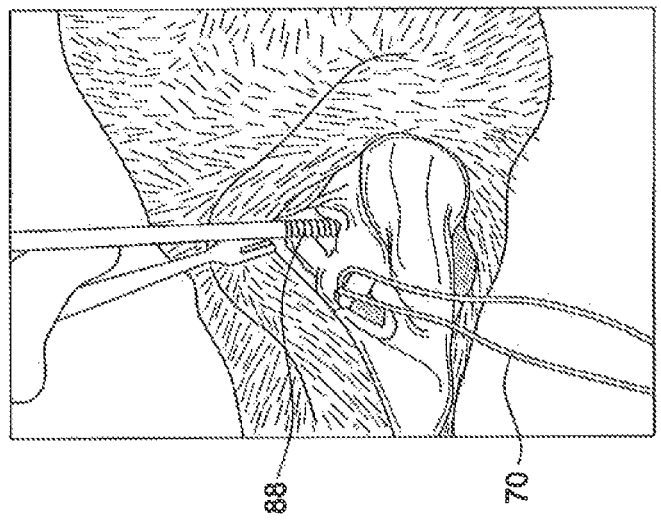
Figure 29A:
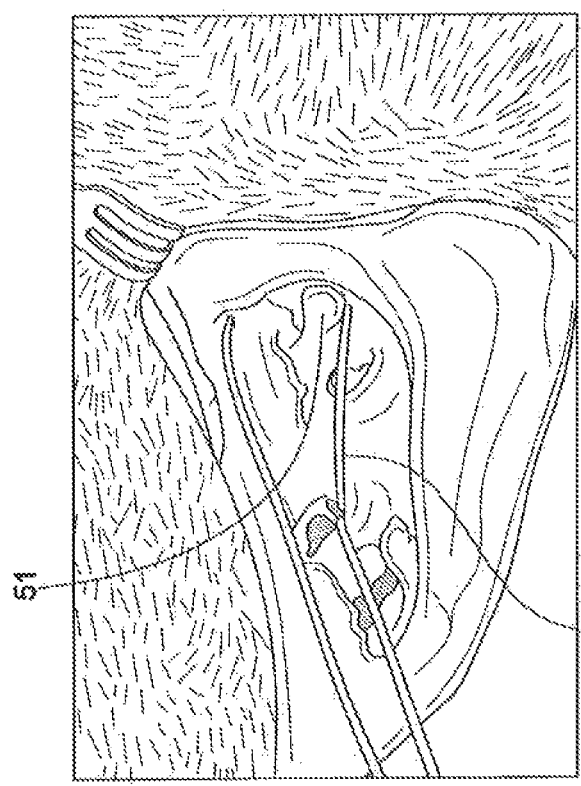
Figure 29B:
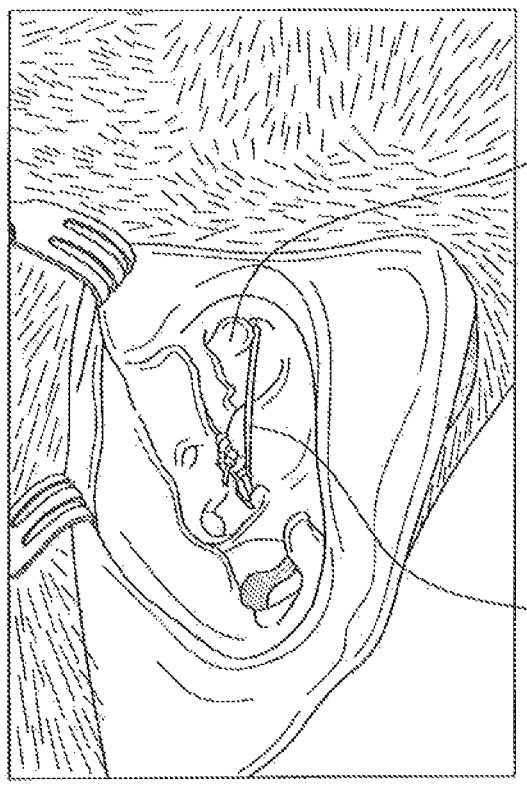

FIG. 22: align C-Ring Guide 60 with suture hole 99 and drill K-wire;

FIGS. 23(a) and 23(b): use 2.7 mm drill 65 over the K-wire;

FIG. 24: feed suture passer 67 through the tunnel;

FIG. 25: pass a flexible strand 70 for example, #5 FiberWire® suture 70, through the suture hole 99;

FIG. 26: pass tails of the #5 FiberWire® 70 through the nitinol loop 67;

FIG. 27: pass suture 70 through the tunnel;

FIGS. 28(a)-(c): fixate the suture 70—first method: use a knotless fixation device 88 such as SwiveLock® 88;

FIGS. 29(a) and 29(b): fixate the suture 70—second method: tie suture 70 around fabella 51;

FIGS. 30(a) and 30(b): fixate the suture 70—third method: use a button 89 on the medial side of femur 53 and attach suture 70 to the button 89;

FIGS. 31(a)-(d): fixate the suture 70—fourth method: use suture holes 99 for fixation of tendons, for example, biceps 80.

Figure 32:
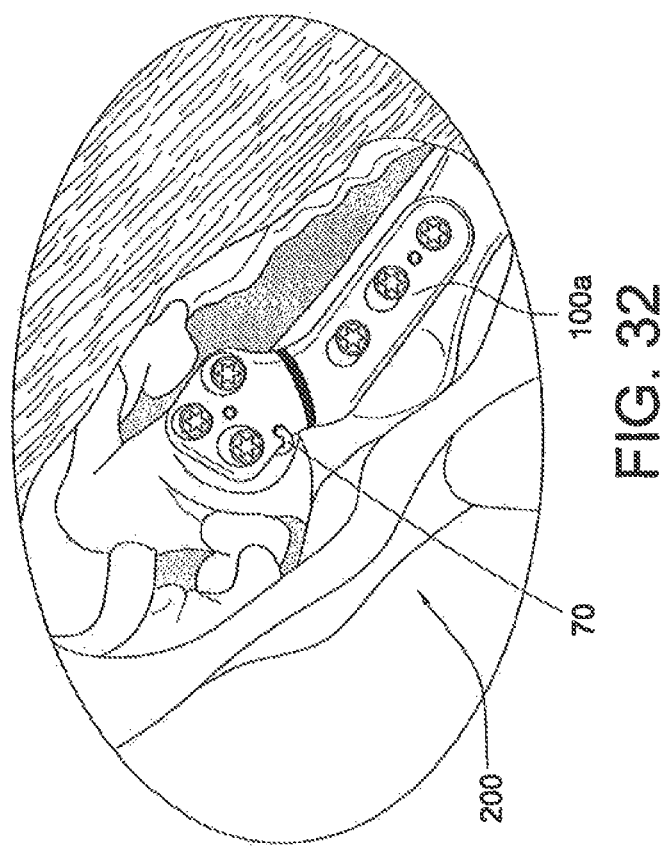

FIG. 32 illustrates a final exemplary TPLO repair 200 of the present invention with exemplary TPLO plate 100a.

The at least one flexible strand 70 may be suture or a high-strength suture, such as FiberWire® suture, which is disclosed and claimed in U.S. Pat. No. 6,716,234, the entire disclosure of which is incorporated by reference in its entirety herein. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The at least one flexible strand 70 may be also suture tape such as FiberTape®, suture chain such as FiberChain®, or a flexible material that is part of a continuous loop/button construct provided with a button and a continuous loop attached to the button. The flexible strand 70 may be also a monofilament, as this works well in veterinarian applications.

In another exemplary embodiment, the flexible strand 70 may be a continuous loop formed of a plurality of suture strands configured to separate from a single strand to a plurality of strands in a continuous loop. In yet another embodiment, the flexible strand is an adjustable loop (forming a TightRope® ACL construct) which consists of two interconnected, adjustable flexible loops formed by splicing a suture strand in a manner disclosed in U.S. Pat. No. 8,460,379 issued on Jun. 11, 2013 and U.S. Pat. No. 8,439,976 issued on May 14, 2013, the disclosures of both of which are incorporated by reference herein in their entireties.

The flexible strand 70 may be also part of a suture loop/needle construct similar to the FiberLoop® construct detailed and disclosed in U.S. Pat. No. 8,298,284 issued on Oct. 30, 2012, the disclosure of which is incorporated by reference herein in its entirety. The flexible strand may be suture tape such as FiberTape® (as disclosed in U.S. Pat. No. 7,892,256) or collagen tape, or combinations thereof.

The fixation devices/implants 25, 88 may have various sizes (various diameters and/or lengths) and may be formed of biocompatible materials such as PEEK, biocomposite materials, metals and/or metal alloys, or combination of such materials, among others. The fixation devices/implants 25, 88 may be also formed of any rigid medically approved materials, for example, plastic or carbon fiber, or combination of different materials.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A surgical apparatus comprising:
a tibial plateau leveling osteotomy plate including a body that includes a proximal region, a distal region, a first surface, and a bone contacting surface opposite the first surface,
wherein a length of the body is sized for a canine proximal tibia,
wherein the bone contacting surface is shaped to conform to a contour of the canine proximal tibia,
wherein a first portion of the length of the body is established by the distal region and a second portion of the length of the body is established by the proximal region,
wherein the first portion of the length is larger than the second portion of the length,
wherein the proximal region is angled relative to the distal region such that the proximal region is offset from either a left-hand side edge or a right-hand side edge of the distal region,
wherein, for a right-hand side offset, both a left-hand side edge and a right-hand side edge of the proximal region are shifted to the right of the left-hand side edge of the distal region, or for a left-hand side offset, both the left-hand side edge and the right-hand side edge of the proximal region are shifted to the left of the right-hand side edge of the distal region, a first plurality of apertures passing through the body and being configured to accommodate a fixation device for fixating the body to the canine proximal tibia; and wherein a longitudinal axis of the body bisects a majority of a length of the distal region and intersects through a first portion of the proximal region, wherein the longitudinal axis intersects a first aperture of a first portion of the first plurality of apertures that are disposed in the proximal region, wherein a second axis intersects each of a second aperture and a third aperture of the first portion of the first plurality of apertures, wherein the second aperture is formed adjacent to a first curved peak of the proximal region and the third aperture is formed adjacent to a second curved peak of the proximal region, wherein the first curved peak establishes a proximal-most tip of the proximal region, wherein the second axis extends at an acute angle relative to the longitudinal axis.

2. The surgical apparatus as recited in claim 1, wherein the first plurality of apertures includes a combination of circular holes and oval holes.

3. The surgical apparatus as recited in claim 1, wherein the body of the tibial plateau leveling osteotomy plate is a rigid body comprised of a metallic material.

4. The surgical apparatus as recited in claim 3, wherein the metallic material is stainless steel.

5. The surgical apparatus as recited in claim 1, comprising a second plurality of apertures passing through the body and configured to accommodate a flexible strand or a k-wire, wherein at least one of the second plurality of apertures is disposed in each of the proximal region and the distal region of the body.

6. The surgical apparatus as recited in claim 1, wherein the second axis intersects through a second portion of the proximal region that is near the first curved peak and through a third portion of the proximal region that is near the second curved peak of the proximal region.

7. The surgical apparatus as recited in claim 1, wherein the distal region protrudes outwardly to a curved peak at a single location of the distal region.

8. The surgical apparatus as recited in claim 1, wherein the body of the tibial plateau leveling osteotomy plate includes a neck region disposed between the proximal and distal regions, and further comprising a depression formed in the neck region.

9. The surgical apparatus as recited in claim 1, wherein the first aperture is formed adjacent to a third curved peak of the proximal region.

10. The surgical apparatus as recited in claim 9, wherein the first curved peak is disposed nearer to a centerline axis of the proximal region than either of the second curved peak and the third curved peak.

11. The surgical apparatus as recited in claim 1, wherein the proximal region is angled at an acute angle relative to the distal region, and further wherein the first portion of the proximal region through which the longitudinal axis intersects is located at a left-hand side or a right-hand side of the proximal region.

12. The surgical apparatus as recited in claim 1, wherein the proximal region extends in a distal-to-proximal direction away from the distal region along a centerline axis that bisects the proximal region into two equal parts, and further wherein the centerline axis intersects the first curved peak.

13. The surgical apparatus as recited in claim 1, wherein the first curved peak is disposed further away from the distal region than the second curved peak.

14. The surgical apparatus as recited in claim 1, wherein the second portion provides less than about ⅓ of the length of the body.

15. The surgical apparatus as recited in claim 1, wherein the proximal region is a proximal end region establishing a tibial plateau leveling head portion of the tibial plateau leveling osteotomy plate, and the distal region is a distal shaft region establishing a shaft portion of the tibial plateau leveling osteotomy plate.

16. The surgical apparatus as recited in claim 1, wherein the first aperture, the second aperture, and the third aperture are substantially equally sized apertures.

17. The surgical apparatus as recited in claim 1, wherein the second axis is closer to parallel than perpendicular relative to the longitudinal axis.

18. A surgical apparatus comprising:
a tibial plateau leveling osteotomy plate including a body that includes a proximal region, a distal region, a first surface, and a bone contacting surface opposite the first surface, wherein a length of the body is sized for a canine proximal tibia, wherein a first portion of the length is established by the distal region and a second portion of the length is established by the proximal region, wherein the first portion of the length is larger than the second portion of the length, wherein the proximal region is angled relative to the distal region such that the proximal region is offset from either a left-hand side edge or a right-hand side edge of the distal region, wherein, for a right-hand side offset, both a left-hand side edge and a right-hand side edge of the proximal region are shifted to the right of the left-hand side edge of the distal region, or for a left-hand side offset, both the left-hand side edge and the right-hand side edge of the proximal region are shifted to the left of the right-hand side edge of the distal region, wherein the proximal region protrudes outwardly to a curved peak at least at two different locations of the proximal region where a perimeter of the proximal region experiences a change in direction;

a first plurality of apertures passing through the body and being configured to accommodate a fixation device for fixating the body to the canine proximal tibia; and wherein a longitudinal axis of the body bisects a majority of a length of the distal region, wherein the longitudinal axis intersects through a first portion of the proximal region that is near a first curved peak of the proximal region, wherein a second axis intersects each of a first aperture and a second aperture of a first portion of the first plurality of apertures that are disposed in the proximal region, wherein the second axis is closer to parallel than perpendicular relative to the longitudinal axis, wherein the first aperture is formed adjacent to a second curved peak of the proximal region and the second aperture is formed adjacent to a third curved peak of the proximal region, wherein the proximal region extends in a distal-to-proximal direction away from the distal region along a centerline axis that bisects the proximal region into two equal parts, wherein the centerline axis intersects the second curved peak, wherein the longitudinal axis intersects a third aperture of the first portion of the first plurality of apertures, wherein the third aperture is formed adjacent to the first curved peak of the proximal region, wherein the second curved peak is disposed between the first curved peak and the third curved peak along an edge of the body, wherein the first aperture, the second aperture, and the third aperture are substantially equally sized apertures.

19. A surgical apparatus comprising:

a tibial plateau leveling osteotomy plate including a body that includes a proximal region, a distal region, a first surface, and a bone contacting surface opposite the first surface, wherein a length of the body is sized for a canine proximal tibia, wherein a first portion of the length of the body is established by the distal region and a second portion of the length of the body is established by the proximal region, wherein the first portion of the length is larger than the second portion of the length, wherein the proximal region is angled at an acute angle relative to the distal region such that the proximal region is offset from either a left-hand side edge or a right-hand side edge of the distal region, wherein, for a right-hand side offset, both a left-hand side edge and a right-hand side edge of the proximal region are shifted to the right of the left-hand side edge of the distal region, or for a left-hand side offset, both the left-hand side edge and the right-hand side edge of the proximal region are shifted to the left of the right-hand side edge of the distal region;

a first plurality of apertures passing through the body and being configured to accommodate a fixation device for fixating the body to the canine proximal tibia;

wherein a longitudinal axis of the body bisects a majority of a length of the distal region and intersects through a first portion of the proximal region, wherein the first portion of the proximal region through which the longitudinal axis intersects is located at a left-hand side or a right-hand side of the proximal region, wherein the longitudinal axis intersects a first aperture of a first portion of the first plurality of apertures that are disposed in the proximal region, wherein a second axis intersects each of a second aperture and a third aperture of the first portion of the first plurality of apertures, wherein the second aperture is formed adjacent to a first curved peak of the proximal region and the third aperture is formed adjacent to a second curved peak of the proximal region, wherein the second axis extends at an acute angle relative to the longitudinal axis; and a second plurality of apertures passing through the body and configured to accommodate a flexible strand or a k-wire, wherein at least one of the second plurality of apertures is disposed in each of the proximal region and the distal region of the body.

* * * * *